(12) United States Patent
Holländer et al.

(10) Patent No.: US 11,542,494 B2
(45) Date of Patent: Jan. 3, 2023

(54) METHOD FOR ISOLATING A TARGET NUCLEIC ACID INCLUDING SMALL TARGET NUCLEIC ACIDS WITH HIGH YIELD

(75) Inventors: Vera Holländer, Unna (DE); Gabriele Christoffel, Cologne (DE); Martin Schlumpberger, Hilden (DE)

(73) Assignee: QIAGEN GmbH, Hilden (DE)

( * ) Notice: Subject to any disclaimer, the term of this patent is extended or adjusted under 35 U.S.C. 154(b) by 0 days.

(21) Appl. No.: 13/820,228

(22) PCT Filed: Sep. 2, 2011

(86) PCT No.: PCT/EP2011/065240
§ 371 (c)(1),
(2), (4) Date: Mar. 1, 2013

(87) PCT Pub. No.: WO2012/028737
PCT Pub. Date: Mar. 8, 2012

(65) Prior Publication Data
US 2013/0164825 A1     Jun. 27, 2013

(30) Foreign Application Priority Data
Sep. 2, 2010   (EP) .................................. 10009130

(51) Int. Cl.
C12Q 1/68      (2018.01)
C12N 15/10     (2006.01)
C07H 21/04     (2006.01)

(52) U.S. Cl.
CPC ..... C12N 15/1006 (2013.01); C12N 15/1017 (2013.01)

(58) Field of Classification Search
None
See application file for complete search history.

(56) References Cited

U.S. PATENT DOCUMENTS

| | | | | |
|---|---|---|---|---|
| 5,182,205 A * | 1/1993 | Bauer et al. | ........... | C07K 14/47 435/252.3 |
| 5,973,138 A * | 10/1999 | Collis | ................ | C12N 15/1013 435/6.16 |
| 6,180,778 B1 * | 1/2001 | Bastian | .............. | C12N 15/1006 536/25.3 |
| 10,273,470 B2 | 4/2019 | Holländer et al. | | |
| 2007/0249821 A1* | 10/2007 | Bitner et al. | ........... | C07H 21/00 536/25.4 |
| 2009/0081802 A1* | 3/2009 | Ritt et al. | ............. | C12N 15/101 436/94 |
| 2009/0202998 A1 | 8/2009 | Schlumpberger et al. | | |
| 2009/0298129 A1* | 12/2009 | Spence et al. | ............... | 435/91.2 |
| 2010/0291658 A1 | 11/2010 | Holländer et al. | | |

FOREIGN PATENT DOCUMENTS

| | | | | |
|---|---|---|---|---|
| EP | 0 880 537 B1 | 12/2004 | | |
| WO | 95/21849 A1 | 8/1995 | | |
| WO | WO 9521849 A1 * | 8/1995 | ......... | C12N 15/1006 |
| WO | WO-9521849 A1 * | 8/1995 | ......... | C12N 15/1006 |
| WO | 98/59076 A1 | 12/1998 | | |

OTHER PUBLICATIONS

Macherey-Nagel GmbH & Co., Isolation of small and large RNA, User Manual, NucleoSpin® miRNA, Oct. 2009/Rev. 01, XP-002606772, 50 pages.
Macherey-Nagel GmbH & Co., RNA Purification Products, NucleoSpin® miRNA, Oct. 2009/Rev. 01, XP-002606773, 4 pages.
Roche Diagnostics GmbH, High Pure miRNA Isolation Kit, Ver. Jul. 2009, Cat. No. 05 080 576 001, XP-002606774, 24 pages.
Ambion, Inc., mirVana™ miRNA Isolation Kit (Part No. AM1560, AM1561), Protocol, 2008, XP-002606775, 30 pages.
Invitrogen, Inc., PureLink™ miRNA Isolation Kit, Instruction Manual, Ver. C, Jul. 18, 2005, Catalog No. K1570-01, XP-002606776, 33 pages.
Norgen Biotek Corp., microRNA Purification Kit, Product #21300, Product Insert, 2009, XP-002606777, 14 pages.
Qiagen GmbH, miRNeasy Mini Handbook, Oct. 2007, XP-002606778, 50 pages.
Bantle et al., "Specificity of Oligo (dT)-Cellulose Chromatography in the Isolation of Polyadenylated RNA," *Analytical Biochemistry* 72:413-427 (1976).

* cited by examiner

*Primary Examiner* — Bradley L. Sisson
(74) *Attorney, Agent, or Firm* — Seed IP Law Group LLP

(57) ABSTRACT

The present invention pertains to a method for isolating a target nucleic acid including small target nucleic acids from a sample, said method comprising at least the following steps a) binding at least a portion of the target nucleic acid including small target nucleic acids to a nucleic acid binding solid phase comprised in a column by passing the sample through said column, b) performing an enzymatic and/or chemical treatment on the nucleic acid binding solid phase while the target nucleic acid is bound to said solid phase, c) collecting at least a portion of the small target nucleic acids released from the solid phase during said treatment of step b) as flow-through, d) contacting said flow-through which comprises small target nucleic acids mixed with a recovery solution with a nucleic acid binding solid phase for binding the contained small target nucleic acids to said nucleic acid binding solid phase, e) optionally performing an elution. The present invention results in a considerable increase in the yield of small target nucleic acids in the isolated target nucleic acid because it allows to efficiently capture and recover small target nucleic acids.

27 Claims, 6 Drawing Sheets

METHOD FOR ISOLATING A TARGET NUCLEIC ACID INCLUDING SMALL TARGET NUCLEIC ACIDS WITH HIGH YIELD

The present invention pertains to a method for isolating a target nucleic acid, including small target nucleic acids, from a sample and in particular provides means for efficiently isolating small target nucleic acids with high yield from a sample.

The study of small nucleic acids in the order of 1000 or 500 nucleotides or less from various tissues, body fluids and organisms is an area of extreme interest and promises to remain one for the future. Small nucleic acids in particular include but are not limited to small RNAs such as inter alia micro RNAs (miRNA) and small interfering RNA molecules both of which can have a powerful effect on the expression of a gene. Furthermore, also other small nuclear and small nucleolar RNAs (e.g. snRNAs and snoRNAs) involved in mRNA and rRNA processing are of interest as well as small DNA molecules. Furthermore, nucleic acids having a length of 1000 or 500 nucleotides or less are also often contained as degradation products in special samples such as e.g. samples that have been formalin fixed and paraffin-embedded (FFPE samples), because the respective preservation may compromise the DNA and/or RNA integrity.

With the increasing interest in respective small nucleic acids, the standard isolation procedures have been modified to facilitate the isolation of small nucleic acids and in particular to improve the yield of small nucleic acids. This, as the known protocols used as standard to isolate DNA or RNA are usually not ideal for isolating small nucleic acids because the small nucleic acids are often not effectively captured and eluted during the isolation process using the standard methods. Therefore, the target nucleic acids isolated from samples using standard procedures usually do not comprise the small target nucleic acids in sufficient amounts and thus provide acceptable yields because the small nucleic acids are either not bound or get lost during the nucleic acid isolation procedure. Thus, there is a need for improved techniques for the efficient isolation of small target nucleic acids either alone or as a portion of the isolated total target nucleic acid such as e.g. total RNA or total DNA.

Methods that have been optimized for the isolation of small nucleic acids often rely on phenol and chloroform extraction and stepwise alcohol fractionation. According to one embodiment, the RNA is concentrated in the aqueous phase and is then subsequently isolated therefrom e.g. by adding at least one alcohol and binding the RNA to a membrane. Here, it is also important to efficiently capture the small RNAs in the isolated total RNA.

Furthermore, methods for isolating small nucleic acids such as small RNAs have been developed which involve the use of chaotropic agents, high concentrations of alcohol and nucleic acid binding columns which comprise e.g. a nucleic acid binding membrane such as a silica membrane. Total RNA isolated with these protocols comprises small RNAs, if respective small RNAs are contained in the sample. Respective membrane-based isolation protocols are in particular suitable for isolating small nucleic acids either alone or as a portion of the total target nucleic acid from various samples.

However, many nucleic acid isolation procedures that use a column based solid phase for binding the nucleic acids (e.g. a nucleic acid binding membrane comprised in a column) involve one or more treatment steps involving one or more aqueous solutions while the target nucleic acid is bound to the nucleic acid binding phase (also called e.g. "on-membrane" or "on-column" treatment steps). Examples of respective treatment steps that are performed while the nucleic acids are bound to the nucleic acid binding solid phase include but are not limited to protein digestion steps and nuclease digestion steps such as e.g. DNase or RNase treatments. It was found that the performance of respective treatment steps decreases the yield of target nucleic acids and in particular decreases the yield of small target nucleic acids because said treatments have the effect that at least a portion of the bound target nucleic acid and in particular the small target nucleic acid is released from the nucleic acid binding solid phase during said treatment steps. Thus, to prevent that released nucleic acids get lost in the subsequent washing or processing steps, it was known in the prior art to apply e.g. a chaotropic solution (e.g. a chaotropic washing solution) that restores suitable binding conditions after the treatment was performed in order to restore the binding of the potentially released target nucleic acids to the nucleic acid binding phase. A respective restoration step is e.g. described in WO 98/59076 and is also used in many commercially available nucleic acid isolation kits.

However, it was found that despite performing a respective restoration step for restoring the binding of potentially released target nucleic acids to the nucleic acid binding solid phase, small target nucleic acids get eventually lost during the isolation process. This particularly is the case when isolating the nucleic acids using a column based solid phase for binding the nucleic acids, e.g. when using columns comprising a nucleic acid binding membrane. Thus, there is still a need for improvement in order to increase the yield of small nucleic acids in the isolated target nucleic acid.

Thus, it is the object of the present invention to provide a method for isolating at least one target nucleic acid which includes or may consists of small target nucleic acids, wherein the yield of the small target nucleic acids is increased.

SUMMARY OF THE INVENTION

The present invention is based on the finding that the application of a restoration buffer or a binding-enhancing washing buffer after performing e.g. an enzymatic treatment while the nucleic acids are bound to the nucleic acid binding solid phase is insufficient for re-capturing and thus isolating small target nucleic acids that were released during said treatment with acceptable yield if using a column based nucleic acid binding solid phase. Subsequently, this will be explained based on the preferred embodiment, wherein a nucleic acid binding membrane is used as solid phase. Without being bound by theory it is assumed that at least a portion of the small target nucleic acids released during the on-membrane treatment is located beneath the membrane and/or far down the pores of the membrane. Respective "escaped" small target nucleic acids can not be efficiently re-bound by the application of a restoration buffer (or a binding enhancing washing buffer) because they are not in contact with the nucleic acid binding area of the membrane and accordingly, get lost in the subsequent processing steps. Similar problems arise when using other column based nucleic acid binding solid phases, in particular if the nucleic acid binding solid phase only forms e.g. a thin layer in the column. The present invention teaches to collect these "escaped" small target nucleic acids and to bind them to a nucleic acid binding solid phase. Thereby, also these "escaped" small target nucleic acids (that are lost when performing the prior art methods) can be efficiently captured in the target nucleic acid isolation process, thereby increasing the yield of small target nucleic acids in the isolated target nucleic acid. The method according to the present invention thus allows the isolation of small target nucleic acids with improved yield and thereby provides considerable advantages over the methods known in the prior art.

Thus, according to a first aspect, a method for isolating at least one target nucleic acid including small target nucleic acids from a sample is provided, said method comprising at least the following steps
  a) binding at least a portion of the target nucleic acid including small target nucleic acids to a nucleic acid binding solid phase comprised in a column by passing the sample through said column,
  b) performing an enzymatic and/or chemical treatment on the nucleic acid binding solid phase while the target nucleic acid is bound to said solid phase,
  c) collecting at least a portion of the small target nucleic acids released from the solid phase during said treatment of step b) as flow-through,
  d) contacting said flow-through which comprises small target nucleic acids mixed with a recovery solution with a nucleic acid binding solid phase for binding the contained small target nucleic acids to said nucleic acid binding solid phase,
  e) optionally performing an elution.

According to one aspect, a method for isolating at least one target nucleic acid including small target nucleic acids from a sample is provided, said method comprising at least the following steps
  a) binding at least a portion of the target nucleic acid including small target nucleic acids to a nucleic acid binding membrane by passing the sample through said membrane,
  b) performing a treatment involving an aqueous solution on the membrane while the target nucleic acid is bound to said membrane,
  c) passing a recovery solution through said membrane and collecting the flow-through which comprises small target nucleic acids,
  d) passing said flow-through through the membrane of step a) for re-binding the contained small target nucleic acids to said membrane,
  e) optionally eluting the target nucleic acid including the small nucleic acid from said membrane.

Furthermore, the present invention pertains to the use of a recovery solution capable of binding small nucleic acids to a nucleic acid binding solid phase comprised in a column, for re-binding small nucleic acids that were released from said nucleic acid binding solid phase during a treatment that was previously performed while the nucleic acids were bound to said solid phase and that were collected preferably as flow-through.

Furthermore, the present invention pertains to a kit for performing the methods according to the present invention which comprises:
  a) a nucleic acid binding solid phase, preferably a membrane, comprised in a column;
  b) a binding buffer for binding a target nucleic acid including small target nucleic acids to said nucleic acid binding solid phase comprising a chaotropic agent and an alcohol;
  c) a recovery solution comprising a chaotropic agent in a concentration of 0.5M up to the saturation limit and an alcohol in a concentration of at least 50%; and
  d) instructions for performing the method according to the present invention.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

BRIEF DESCRIPTION OF THE FIGURES

In FIG. 8a, for all samples the same template volumina, in FIG. 8b the same template concentrations have been used.

The diagrams in FIG. 9a and FIG. 9b show the results of a realtime PCR experiment in order to analyze Madh7 RNA (see example 7). RNA has been purified from FFPE samples derived from 3 different rat tissues: 1. liver (embedded for 2 months), 2. kidney (embedded for 19 months) and 3. lung (embedded for 8 months).

DETAILED DESCRIPTION OF THE INVENTION

Figure 1:
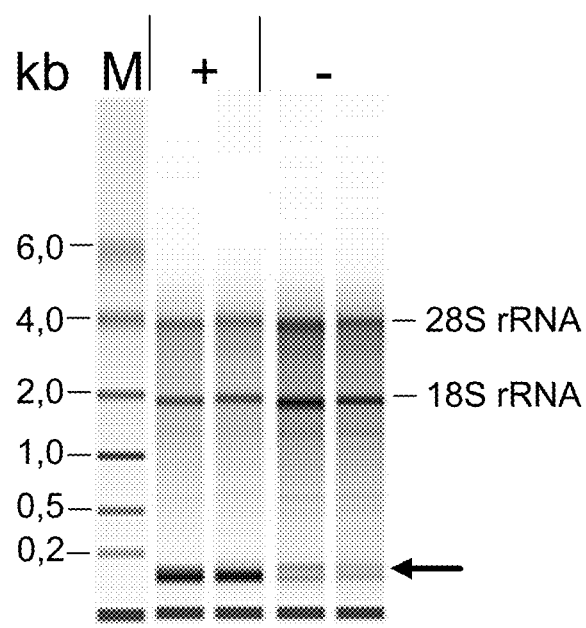
FIGS. 1 to 3 show the size distribution of RNA isolated from kidney tissue using an Agilent Bio Analyzer. "+" characterizes the RNA that was isolated using the method according to the present invention and "−" characterizes the RNA that was isolated using the reference method. The small RNA fraction is marked with an arrow.

It was surprisingly found that the yield of small target nucleic acids can be considerably increased in a method for isolating at least one target nucleic acid including small target nucleic acids from a sample, when at least the following steps are performed:
  a) binding at least a portion of the target nucleic acid including small target nucleic acids to a nucleic acid binding solid phase comprised in a column by passing the sample through said column, b) performing an enzymatic and/or chemical treatment on the nucleic acid binding solid phase while the target nucleic acid is bound to said solid phase, c) collecting at least a portion of the small target nucleic acids released from the solid phase during said treatment of step b) as flow-through, d) contacting said flow-through which comprises small target nucleic acids mixed with a recovery solution with a nucleic acid binding solid phase for binding the contained small target nucleic acids to said nucleic acid binding solid phase, e) optionally performing an elution.

The individual steps of the method according to the present invention will be explained in further detail below.

In step a), the target nucleic acid including small target nucleic acids that are comprised in the sample is bound to the nucleic acid binding solid phase comprised in a column when the sample passes through said column. Preferably, a nucleic acid binding membrane is used as solid phase. Suitable binding conditions for binding a target nucleic acid including the small target nucleic acids to a nucleic acid binding solid phase such as a membrane are known in the prior art and are also described in further detail below. The binding conditions also depend on the target nucleic acid to be isolated (e.g. RNA or DNA or both). Preferably, binding conditions are used that allow strong and thus efficient binding of the target nucleic acids including the small target nucleic acids to the nucleic acid binding solid phase in order to allow the isolation of the target nucleic acid including the small target nucleic acids with high yield. To achieve suitable binding conditions in step a), the sample can be mixed with a suitable binding solution such as a binding buffer that establishes the desired binding conditions. Commonly, step a) will be performed after the initial lysis of the sample in case a sample is processed that needs lysis. Furthermore, also other pretreatment steps can be performed prior to step a), e.g. in order to clear the lysate, to remove non-target nucleic acids or other contaminants, to concentrate the target nucleic acids and/or to pre-purify the target nucleic acids. In these cases, the respectively pretreated or processed sample is passed as sample through the column in step a) and at least the target nucleic acids including the small target nucleic acids bind to the nucleic acid binding solid phase. In case a chemical lysis solution is used for lysis, said lysis solution can also contribute to establish the appropriate binding conditions.

In step b), an enzymatic and/or chemical treatment is performed on the solid phase while the target nucleic acid including small target nucleic acids is bound to said solid phase, e.g. an on-membrane treatment in case a membrane is used as nucleic acid binding solid phase. Respective treatments are commonly performed during a nucleic acid isolation procedure and include but are not limited to treatments selected from the group consisting of a nuclease digestion step, e.g. an DNase or RNase treatment, a protein digestion step, e.g. a treatment with a proteolytic enzyme for degrading protein contaminations that were bound e.g. to a membrane during binding step a) (see e.g. WO 2009/016110, herein incorporated by reference), a lipase treatment and a target nucleic acid modification step. Respective treatments usually involve the use of one or more aqueous solutions having a composition that allows or promotes the performance of the desired treatment. However, said aqueous solution(s) usually do(es) not have a composition allowing or promoting binding of the target nucleic acid and in particular the small target nucleic acids to said nucleic acid binding solid phase. This particularly applies when performing e.g. an on-membrane or an on-column enzymatic treatment because conditions must be established allowing the enzyme to be active. Therefore, the enzymatic and/or chemical treatment performed in step b) usually involves conditions that results at least in a partial release of small target nucleic acids from the nucleic acid binding solid phase. Thus, the addition of the aqueous solution during the treatment performed in step b) results in a partial release of the target nucleic acids that were bound in step a) to the nucleic acid binding solid phase. The smaller the target nucleic acid, the higher the risk that said target nucleic acid completely dissociates from the nucleic acid binding solid phase during the treatment performed in step b). As discussed above, respectively released target nucleic acids (which usually are small in size) can be located above, in or beneath the membrane (respectively the nucleic acid binding solid phase comprised in the column). In case the released target nucleic acids are located e.g. beneath the membrane or far down the pores of the membrane, they can not be efficiently re-captured by applying a restoration solution or by using a binding enhancing washing buffer. Accordingly, they get lost during the further processing of the sample as is the case in the methods according to the prior art.

In order to capture and thus isolate respectively "escaped" small target nucleic acids that can not be re-bound by restoring suitable binding conditions, the present invention teaches to remove in step c) the "escaped" small target nucleic acids from the nucleic acid binding solid phase. Thus, in step c) at least a portion of the small target nucleic acids that were released from the nucleic acid binding solid phase during said treatment of step b) is collected as flow-through. Preferably, most or all of the "escaped" small target nucleic acids are respectively collected. Performing said collection step c) is essential, because it considerably increases the yield of small target nucleic acids in the isolated target nucleic acid as is also demonstrated by the examples. Of course, thereby, also larger target nucleic acids that might have been released during step b) can be efficiently collected. However, as discussed above, this problem occurs less often with larger target nucleic acids because larger target nucleic acids usually bind stronger to the nucleic acid binding solid phase than smaller target nucleic acids. However, if they are released, they are also efficiently re-captured by the method according to the present invention.

In step d), said flow-through comprising the small target nucleic acids mixed with a recovery solution (and optionally further solutions/chemicals) is contacted with a nucleic acid binding solid phase for binding the contained small target nucleic acids to said solid phase. By mixing the small target nucleic acids with the recovery solution according to the present invention, binding conditions are established that allow binding the collected small target nucleic acids to the solid phase. The nucleic acid binding solid phase used in step d) for binding the small target nucleic acid is preferably the same nucleic acid binding solid phase that is used in step a). In this embodiment, the flow-through comprising the small target nucleic acids mixed with a recovery solution is re-applied to the nucleic acid binding solid phase that was used in step a), thereby re-binding the small target nucleic acids to said solid phase and joining the small target nucleic acids with the target nucleic acids that were not released in step b). As discussed above, preferably a membrane is used in step a) as nucleic acid binding solid phase. However, it is also within the scope of the present invention to use a different nucleic acid binding solid phase in step d), such as e.g. magnetic silica particles, a different column based nucleic acid binding solid phase or the same type of membrane that was used in step a). This recovery of the "escaped" small target nucleic acids performed in step d) allows to considerably reducing the loss of small target nucleic acids and thus increases the yield of small target nucleic acids in the isolated target nucleic acid.

In optional step e), one or more elution steps are performed. Alternatively or additionally, the target nucleic acid may also be processed while being bound to the solid phase, depending on the intended downstream application, respectively the intended use of the target nucleic acid. In case it is desired to perform an elution step, elution can be performed for example by using classical elution solutions such as water, elution buffers, low-salt buffers and in particular biological buffers. Preferably, an elution solution is used that does not interfere with the intended downstream application. However, it is also within the scope of the present invention to release and thus elute the target nucleic acids if desired by other elution means such as e.g. heating. In case a solid phase is used in step d) that differs from the nucleic acid binding solid phase used in step a), it is within the scope of the present invention to elute the target nucleic acid from the solid phase used in step a) and to separately elute the small target nucleic acids that were bound to the solid phase used in step d) and to combine the respective eluates. It is also within the scope of the present invention to combine the solid phases prior to performing the elution step. Furthermore, it is also within the scope of the present invention to repeat the elution step in order to ensure that all target nucleic acids are efficiently released from the nucleic acid binding phase.

As is shown by the examples, the method according to the present invention which in contrast to the prior art additionally performs steps c) and d) when using a column based nucleic acid isolation procedure considerably increases the yield of small target nucleic acids in the isolated target nucleic acid.

There are several options for performing step c) and d) for capturing and thus isolating the "escaped" small target nucleic acids. Some non-limiting embodiments are described in further detail below.

According to one embodiment, in step c), a recovery solution which establishes conditions suitable for binding small nucleic acids to the nucleic acid binding solid phase that was used in step a) is passed through the column and the flow-through which comprises the "escaped" small target nucleic acids is collected. Said flow-through, which is already mixed with the recovery solution (and which can optionally be mixed with further ingredients) is applied in step d) to the same nucleic acid binding solid phase that was used in step a). Thereby, the "escaped" small target nucleic acids contained in the flow-through are bound to the solid phase that was used in step a) (and to which the target nucleic acids that were not released during the on-membrane treatment performed in step b) are still bound). This embodiment is preferred, because it has several advantages. First, passing a recovery solution through said column and accordingly through the comprised nucleic acid binding solid phase establishes, respectively re-establishes conditions suitable for binding small nucleic acids to the nucleic acid binding solid phase. Thereby, it is ensured that target nucleic acids and in particular the small target nucleic acids that were at least partially released during the treatment of step b) but which can still be re-bound to the solid phase are efficiently re-bound to said solid phase because the recovery solution re-establishes appropriate binding conditions. Second, "escaped" small target nucleic acids that can not be re-bound to the solid phase by re-establishing appropriate binding conditions are efficiently removed and thus collected as flow-through in the recovery solution. Third, directly using the recovery solution in step c) for collecting the "escaped" small target nucleic acids has the advantage that the small target nucleic acids are directly provided in a solution providing appropriate binding conditions for re-binding the "escaped" small target nucleic acids to the solid phase that was used in step a) for binding the target nucleic acids including the small target nucleic acids. Thereby, the "escaped" small target nucleic acids can be re-joined with the target nucleic acids that are still bound to said solid phase and thus, all target nucleic acids can be processed together in the subsequent preparation steps.

According to a further embodiment for collecting the escaped target nucleic acids, the enzymatic and/or chemical treatment performed in step b) comprises the use of an aqueous solution and the "escaped" small target nucleic acids are saved by collecting the flow-through which comprises the small target nucleic acids and the aqueous solution that was used for the treatment in step b). In this embodiment, the recovery solution can be added to the flow-through after it was collected in step c) and the obtained mixture, optionally mixed with further additives, is contacted in step d) with a nucleic acid binding solid phase, which preferably is the nucleic acid binding solid phase that was used in step a) as is described above.

According to one embodiment, an aqueous solution, e.g. a reaction buffer, water or an elution buffer is applied to and passed through the column which comprises the nucleic acid binding solid phase, which preferably is a membrane. The released small target nucleic acids are then collected in said aqueous solution. If desired, an enzymatic and/or chemical treatment of the respectively collected small target nucleic acids can be performed and it is also within the scope of the present invention to add further compositions/substances to the collected small target nucleic acids. Furthermore, an enzymatic and/or chemical treatment of the target nucleic acids that are still bound to the solid phase used in step a) can be performed. This embodiment has the advantage in that it allows treating the bound (usually larger) target nucleic acids differently from the pre-eluted and collected small target nucleic acids.

According to one aspect, a method for isolating a target nucleic acid including small target nucleic acids from a sample is provided, said method comprising at least the following steps
  a) binding at least a portion of the target nucleic acid including small target nucleic acids to a nucleic acid binding membrane by passing the sample through said membrane,
  b) performing a treatment involving an aqueous solution on the membrane while the target nucleic acid is bound to said membrane,
  c) passing a recovery solution through said membrane and collecting the flow-through which comprises small target nucleic acids,
  d) passing said flow-through through said membrane of step a) for re-binding the contained small target nucleic acids to said membrane,
  e) optionally eluting the target nucleic acid including the small nucleic acid from said membrane. Preferably, the target nucleic acids including the small target nucleic acids are eluted from the membrane.

Any suitable method can be used in step c) for collecting at least a portion of the small target nucleic acids as flow-through. Suitable collection methods utilized when performing a column based nucleic acid isolation procedure include but are not limited to performing a centrifugation step, applying a positive or negative pressure in order to press and/or suck the small target nucleic acids, which are preferably comprised in a recovery solution or an aqueous solution as described above, in either direction through the nucleic acid binding solid phase comprised in the column, wherein said solid phase preferably is a membrane.

The recovery solution that is used for re-binding the "escaped" small target nucleic acids should provide respectively establish conditions suitable for binding small nucleic acids to the nucleic acid binding solid phase used in step d). The recovery solution may also be obtained by mixing one or more solutions and/or ingredients. The recovery solution may provide conditions suitable for binding total nucleic acids including small nucleic acids to the nucleic acid binding solid phase used in step d). In case a specific target nucleic acid is to be isolated, the recovery solution may provide conditions suitable for preferably binding the desired type of target nucleic acid (e.g. total RNA including small RNA) to the nucleic acid binding solid phase used in step d). It may also provide conditions suitable for binding DNA (e.g. total DNA, genomic DNA, fragmented DNA and/or low molecular weight DNA such as plasmid DNA) including small DNA to the nucleic acid binding solid phase used in step d), in case DNA is the desired target nucleic acid. The binding conditions provided by the recovery solution and/or the mixture of the recovery solution and the flow-through collected in step c) can be the same or similar to the conditions that are used in step a) for binding the target nucleic acids including the small target nucleic acids to the nucleic acid binding solid phase comprised in the column. However, preferably, the recovery solution respectively the binding conditions that are used in step d) are stronger than the binding conditions used in step a).

Preferably, the recovery solution, which may also be obtained by mixing one or more solutions or chemical agents, comprises at least one chaotropic agent and/or at least one alcohol.

Any chaotropic agent can be used for that purpose that causes disorder in a protein or nucleic acid by, for example, but not limited to altering the secondary, tertiary or quaternary structure of a protein or a nucleic acid while leaving the primary structure intact. Preferably, the chaotropic agent is selected from the group consisting of guanidinium hydrochloride, guanidinium thiocyanate, guanidinium isothiocyanate, sodium thiocyanate, sodium iodide, sodium perchlorate, sodium trichloroacetate, sodium trifluoroacetate and urea. Preferably, a chaotropic salt is used. In particular, guanidinium hydrochloride and/or guanidinium thiocyanate can be used as chaotropic agent.

The concentration of the at least one chaotropic agent in the recovery solution and/or in the binding mixture that is used in step d) may lie in a range of 0.05M up to the saturation limit. Preferred concentration ranges lie, depending on the chaotropic agent used, in the range of about 0.1M to 6M, about 0.2M to 4M, about 0.5 to 3M, and preferably lie in the range of about 0.8 to 2M.

Furthermore, the recovery solution and/or the binding mixture that is used in step d) for binding the collected small target nucleic acids to the nucleic acid binding solid phase may comprise at least one alcohol. As alcohol, it is preferred to use short chained branched or unbranched alcohols with preferably one to 5 carbon atoms. Examples are methanol, ethanol, propanol, isopropanol and butanol. Also mixtures of alcohol can be used. The alcohol is preferably selected from isopropanol and ethanol, particularly well suitable is isopropanol when isolating RNA as target nucleic acid. According to one embodiment, the method according to the present invention does not involve the use of phenol and/or chloroform for binding the nucleic acids. However, phenol and chloroform can be e.g. used for sample preparation and/or sample lysis, e.g. in order to obtain an aqueous phase comprising the target nucleic acids, in particular RNA. E.g. said aqueous phase can also be used as sample in step a) preferably mixed with an alcohol, for binding the target nucleic acids to the membrane as is also demonstrated in the examples.

An alcohol may be comprised in the recovery solution and/or the binding mixture used in step d) in a concentration of 10% v/v to 90% v/v. For isolating a target nucleic acid including small target nucleic acids, it is beneficial to use an alcohol concentration of ≥30% v/v, ≥40% v/v, ≥50% v/v, preferably ≥60% v/v, ≥70%. Preferably, the alcohol concentration lies in a range of about 30% v/v to 90% v/v/ or about 40% v/v to 85%, more preferred in the range of about 60% v/v to 80% v/v.

In step a), binding can be performed under the same or similar conditions as were described above for step d). Thus, the binding conditions used in step a) may have one or more of the following characteristics:

a) the conditions are suitable for binding total nucleic acids including small nucleic acids to the nucleic acid binding solid phase comprised in the column;
b) the conditions are suitable for binding total RNA including small RNAs to the nucleic acid binding solid phase comprised in the column;
c) the conditions are suitable for binding DNA including small DNAs to the nucleic acid binding solid phase comprised in the column;
d) binding occurs in the presence of at least one chaotropic agent and at least one alcohol;
e) binding occurs in the presence of at least one chaotropic agent which is selected from the group consisting of guanidinium hydrochloride, guanidinium thiocyanate, guanidinium isothiocyanate, sodium thiocyanate, sodium iodide, sodium perchlorate, sodium trichloroacetate, sodium trifluoroacetate and urea;
f) binding occurs in the presence of at least one chaotropic agent which is contained in the binding mixture in a concentration selected from 0.1M up to the saturation limit concentration, preferably 0.5 to 6M, more preferred 0.5 to 4M; and/or
g) binding occurs in the presence of at least one alcohol which is selected from the group consisting of alcohols described above for binding step d).

Also additional additives can be used in the binding mixture of step a) and/or step d). E.g. additives can be used which support the lysis of the sample, the degradation of proteins and/or which preserve the target nucleic acid in the binding mixture. Examples include but are not limited to chelating agents, inhibitors, detergents, buffering agents, stabilising agents, alkaline agents, nuclease inhibitors and beta-mercaptoethanol, in particular EDTA, EGTA, salts, such as sodium chloride, ammonium sulfate, ammonium chloride, LiCl or other substances which promote the binding and/or the precipitation of the nucleic acids. Respective additives can be comprised e.g. in the recovery solution and/or the binding solution but may also be added separately. Furthermore, a biological buffer can be used during binding in step a) and/or step d) and accordingly, may also be comprised in the recovery solution. Examples of respective buffers include but are not limited to HEPES, MES, MOPS, TRIS, sodium citrate, sodium acetate and BIS-TRIS Propane.

The pH value used during binding in step a) and or d) preferably lies in a range of 4 to 11, for RNA preferably in a range of about 5 to 8, most preferred 6 to 7.5. For DNA the pH value preferably lies within the range of about 5 to 11, most preferred in the range of about 6 to 10. When isolating both types of nucleic acids as target nucleic acid the pH preferably lies within a range of about 6 and 8. Preferably, the recovery solution comprises a buffer which buffers the pH in the ranges described above. According to one embodiment, the pH of the recovery solution lies within the range of about pH 5 to 11, preferably in the range of about 5.5 to 8; most preferred the recovery solution has a pH in the range of about 5 to 7.5 or about 7. Respective pH values are in particular suitable for isolating RNA as target nucleic acid.

According to one embodiment, one or more washing steps are performed between steps a) and b) and/or after step d) while the target nucleic acids are bound to the solid phase. For this purpose common washing solutions may be used. It is recommended to use washing solutions which do not result in a release of the target nucleic acids including the small target nucleic acids from the nucleic acid binding solid phase. According to one embodiment, the solution used for washing comprises at least one chaotropic agent, at least one alcohol and/or at least one buffering component. It may also comprise a detergent. Chaotropic agents that can be used in the washing solutions include but are not limited to guanidinium hydrochloride, guanidinium thiocyanate, guanidinium isothiocyanate and sodium iodide. Furthermore, chaotropic salts can be used which comprise a chaotropic anion selected form the group consisting of trichloroacetate, perchlorate and trifluoroacetate. Examples of respective chaotropic salts are alkali salts like sodium perchlorate, sodium trichloroacetate and sodium trifluoroacetate. As alcohol, short chained branched or unbranched alcohols with preferably one to 5 carbon atoms can be used for washing, respectively in the washing solution. Examples are methanol, ethanol, propanol, isopropanol and butanol. Preferably, isopropanol and/or ethanol are used.

According to one embodiment, the washing solution comprises at least 30% alcohol and at least 0.5M chaotropic salt, preferably at least 2M chaotropic salt. Furthermore, the washing solution may comprise a detergent. Preferably, ionic and/or non-ionic detergents are used as detergent. Preferably, a non-ionic detergent is used in a concentration of at least 0.1%. A respective washing solution is e.g. suitable for washing RNA.

A further suitable washing solution which can be used alternatively or also in addition (preferably subsequently) to the washing solutions described above comprises an alcohol and a biological buffer. Suitable alcohols and biological buffers are described above. Preferably, isopropanol or ethanol, most preferred ethanol is used for a second washing step. Preferably, ethanol is used in a concentration of at least 30% v/v, preferably at least 50% v/v. The biological buffer is preferably Tris at a pH of approx. 7 to 8. However, also other buffers such as sodium citrate and also other pH values can be used, depending on the isolated target nucleic acid and the processed sample.

A further suitable washing solution which can be used alternatively or also in addition (preferably subsequently) to the washing solutions described above also comprises one or more alcohols and optionally a buffer. Suitable alcohols and biological buffers are described above. Preferably, isopropanol or ethanol, most preferred ethanol is used for an alternative washing step. Preferably, ethanol is used in a concentration of at least 50% v/v, preferably at least 70% or more.

The term "sample" is used herein in a broad sense and is intended to include a variety of sources and compositions that contain nucleic acids. The sample may be a biological sample but the term also includes other, e.g. artificial samples which comprise nucleic acids such as e.g. PCR products or compositions comprising already purified nucleic acids which are e.g. supposed to be further concentrated and/or further purified. Exemplary samples include, but are not limited to, whole blood; blood products; red blood cells; white blood cells; buffy coat; swabs, including but not limited to buccal swabs, throat swabs, vaginal swabs, urethral swabs, cervical swabs, throat swabs, rectal swabs, lesion swabs, abcess swabs, nasopharyngeal swabs, and the like; urine; sputum; saliva; semen; lymphatic fluid; amniotic fluid; cerebrospinal fluid; peritoneal effusions; pleural effusions; fluid from cysts; synovial fluid; vitreous humor; aqueous humor; bursa fluid; eye washes; eye aspirates; plasma; serum; pulmonary lavage; lung aspirates; animal, including human or plant tissues, including but not limited to, liver, spleen, kidney, lung, intestine, brain, heart, muscle, pancreas, cell cultures, as well as lysates, extracts, or materials and fractions obtained from the samples described above or any cells and microorganisms and viruses that may be present on or in a sample and the like. Materials obtained from clinical or forensic settings that contain nucleic acids are also within the intended meaning of the term "sample". Preferably, the sample is a biological sample derived from a human, animal, plant, bacteria or fungi. Preferably, the sample is selected from the group consisting of cells, tissue, bacteria, virus and body fluids such as for example blood, blood products such as buffy coat, plasma and serum, urine, liquor, sputum, stool, CSF and sperm, epithelial swabs, biopsies, bone marrow samples and tissue samples, preferably organ tissue samples such as lung, kidney or liver. Furthermore, the skilled artisan will appreciate that lysates, extracts, or processed materials or portions obtained from any of the above exemplary samples are also within the scope of the term "sample". This in particular includes but is not limited to sample lysates, cleared lysates, pre-extracted sample portions which are e.g. enriched for a certain type of target nucleic acid as is e.g. the case during a phenol/chloroform extraction wherein nucleic acids such as RNA are concentrated in the aqueous phase, purified nucleic acids which are supposed to be further purified and/or concentrated and the like. The term "sample" also includes processed samples such as preserved, fixed and/or stabilised samples. As fixative, cross-linking as well as non-cross-linking fixatives can be used (non-limiting commercial examples include PAXgene Tissue Fixative or carnoys solution). Examples of commercially available stabilisers that can be used for stabilising the sample include but are not limited to RNAlater, AIIprotect Tissue, RNAprotect Cell, RNAprotect Saliva, RNAprotect Bacteria, PAXgene Blood RNA, PAXgene Blood DNA, PAXgene Bone Marrow RNA and QIAsafe.

In particular, the method according to the present invention is useful for isolating target nucleic acids from samples containing degraded or compromised nucleic acids such as e.g. degraded RNA or degraded DNA. Non-limiting examples of such samples include cell containing samples that have been preserved, e.g. formalin fixed and paraffin-embedded (FFPE samples) or other samples that were treated with cross-linking fixatives such as e.g. glutaraldehyde. E.g. biopsy samples from tumors are routinely stored after surgical procedures by FFPE, which may compromise DNA and/or RNA integrity. Respective degraded nucleic acids often have a small size and thus are small nucleic acids. The disclosed method may be advantageously used for isolating target nucleic acids which consist of or comprise small target nucleic acids. E.g. the sample may be a sample which comprises small nucleic acids such as non coding RNA (e.g. snoRNAs or miRNA) or small DNA. Furthermore, the target nucleic acid may consist of or may comprise modified or degraded nucleic acids. The modification or degradation can be e.g. due to treatment with a preservative(s).

The term "nucleic acid" as used herein, in particular refers to a polymer comprising ribonucleosides and/or deoxyribonucleosides that are covalently bonded, typically by phosphodiester linkages between subunits, but in some cases by phosphorothioates, methylphosphonates, and the like. Nucleic acids include, but are not limited to, gDNA; circular DNA; low molecular weight DNA, plasmid DNA; circulating DNA; hnRNA; mRNA; noncoding RNA (ncRNA), including but not limited to rRNA, tRNA, miRNA (micro RNA), siRNA (small interfering RNA), snoRNA (small nucleolar RNA), snRNA (small nuclear RNA) and stRNA (small temporal RNA); fragmented or degraded nucleic acids; PNAs; nucleic acid obtained from subcellular organelles such as mitochondria or chloroplasts; and nucleic acid obtained from microorganisms, parasites, or DNA or RNA viruses that may be present in a biological sample. Synthetic nucleic acid sequences that may or may not include nucleotide analogs that are added or "spiked" into a biological sample are also within the scope of the invention.

The terms "small nucleic acid" and "small nucleic acids" in particular refer to nucleic acids having a length of less than 1000 nt, less than 750 nt, less than 500 nt, less than 400 nt, less than 300 nt, less than 250 nt, less than 200 nt, less than 100 nt or less than 70 nt and include but are not limited to miRNA, siRNA and other short interfering nucleic acids, snoRNAs, snRNAs, tRNA, piRNA, tnRNA, small rRNA, hnRNA, circulating nucleic acids, fragments of genomic DNA or RNA, degraded nucleic acids, ribozymes, viral RNA or DNA, nucleic acids of infectios origin, amplification products, modified nucleic acids, plasmidical or organellar nucleic acids and artificial nucleic acids such as oligonucleotides.

The method according to the present invention pertains to a method for isolating at least a target nucleic acid. The terms "target nucleic acid" and "target nucleic acids" are used herein as synonyms. As becomes apparent from the described examples of samples that can be processed according to the method of the present invention, a sample may comprise more than one type of nucleic acid. Depending on the intended use, it may be desirous to isolate all types of nucleic acids from a sample ((e.g. DNA and RNA which would then both be encompassed by the term target nucleic acid or target nucleic acids) or only certain types or a certain type of nucleic acid (e.g. only RNA but not DNA or vice versa) or RNA and DNA in parallel, i.e. from one sample, but separately from each other. All these variants are within the scope of the present invention. The term "small target nucleic acid" or "small target nucleic acids" (these terms are also used as synonyms) in particular refers to small nucleic acids of the desired target type, e.g. small RNA or small DNA, or both small RNA and small DNA. Furthermore, the expression "a target nucleic acid including small target nucleic acids" not only refers to a target nucleic acid which comprises portions of small target nucleic acids (such as e.g. total RNA or total DNA) but also refers to and encompasses target nucleic acids which consist of small target nucleic acids and accordingly, which do not comprise larger nucleic acids.

The sample may be processed prior to performing the binding step a). E.g. the sample can be disrupted and/or lysed in order to release the nucleic acids contained in the sample. The procedure used depends on the sample the target nucleic acid is supposed to be isolated from and includes but is not limited to mechanical disruption, chemical disruption, the addition of proteolytic enzymes, detergents and the like for achieving disruption, respectively lysis of the sample. The lysate may also be cleared or otherwise processed prior to performing the binding step a). Suitable lysis/disruption methods and lysis buffers are known in the prior art and thus, need no description here. Furthermore, additional process steps can be performed, such as e.g. one or more depletion for removing non-target nucleic acids or other undesired components and/or the nucleic acids or other biomolecules contained in the sample may be modified prior to binding in step a) the target nucleic acid to the column based nucleic acid binding solid phase.

Furthermore, if special samples such as embedded samples are processed according to the method of the present invention it is preferred to include steps to release the nucleic acids and/or the sample from the embedding matrix (e.g. from the paraffin). Furthermore, in case special samples such as fixed and cross-linked samples are processed according to the method of the present invention, it is preferred to include steps to also release the nucleic acids from the fixed sample and thus to e.g. reverse the modifications caused by the fixation step, in particular for removing the cross-links. E.g., additional steps such as heating steps can be performed in case the nucleic acids contained in the sample are e.g. cross-linked e.g. as is the case in FFPE samples. Suitable methods and processing steps to achieve that result and to obtain a sample from which the target nucleic acid can be isolated from are known in the prior art and are also e.g. described in EP 10 001 995.9, PCT/EP2011/000920 and WO 2007/068764, herein incorporated by reference.

According to one embodiment, the sample comprises at least one non-target nucleic acid and at least one target nucleic acid. According to one embodiment, the method according to the present inventions comprises a step that removes at least a portion of non-target nucleic acid. E.g., the non-target nucleic acid can be removed by binding at least a portion of the non-target nucleic acid under appropriate conditions to a solid phase and then separating the non-target nucleic acid bound to the solid phase from the remaining sample comprising the target nucleic acid. This can be achieved e.g. by the addition of a suitable solid phase under conditions wherein mainly the non-target nucleic acids are bound to the solid phase. Suitable methods for selectively removing a non-target nucleic acid from a target nucleic acid are for example described in EP 0 880 537 and WO 95/21849, herein incorporated by reference. Other methods include e.g. a phenol/chloroform extraction e.g. in order to concentrate the RNA in the aqueous phase which is then used, preferably mixed with an alcohol, to bind the RNA to the membrane in step a). Other methods suitable for separating target nucleic acids from non-target nucleic acids, which are in particular useful for separating DNA from RNA when isolating the target nucleic acid (or RNA and DNA in parallel) from a fixed sample such as an FFPE sample, are described in EP 10 001 995.9 and PCT/EP2011/000920, herein incorporated by reference.

When intending to isolate (only) RNA as target nucleic acid, the non-target nucleic acid is usually DNA. In this embodiment, a DNase digest is preferably performed in step b) in order to remove, respectively reduce DNA contaminations. Furthermore, when intending to isolate DNA as target nucleic acid, an RNase digest can be performed as step b) in order to remove, respectively reduce RNA contaminations. When using a membrane as nucleic acid binding solid phase, respective on-membrane treatments result in that a considerable amount of the target nucleic acids and in particular the small target nucleic acids is released. As described above and in the example the other non-target nucleic acid can also be isolated in parallel.

According to one embodiment, the sample comprises at least one target nucleic acid and at least one non-target biomolecule, like e.g. proteins, lipids, carbohydrates or metabolites. According to one embodiment, the method according to the present inventions comprises a step that removes at least a portion of the non-target biomolecules. E.g., the non-target biomolecule can be removed by binding at least a portion of the non-target biomolecule under appropriate conditions to a solid phase and then separating the non-target biomolecule bound to the solid phase from the remaining sample comprising the target nucleic acid. This can be achieved e.g. by the addition of a suitable solid phase under conditions wherein mainly the non-target biomolecules are bound to the solid phase. Other methods suitable for separating target nucleic acids from non-target biomolecules, include the removal of the non-target biomolecules by chemical or enzymatic reactions, which can also be done on the membrane e.g. during step b) (see e.g. DE 10 2007 035 250).

Suitable DNase and RNase enzymes and other enzymes effecting e.g. non-target biomolecules as well as buffers and solutions that can be used for performing a respective enzymatic treatment in step b) are known in the prior art and thus, need no detailed description.

The present invention involves in step a) the use of a nucleic acid binding solid phase that is comprised in a column. The term "column" as used herein in particular describes a container having at least two openings. Thereby, a solution and/or sample can pass through said column. The term "column" in particular does not imply any restrictions with respect to the shape of the container which can be e.g. round or angular and preferably is cylindrical. However, also other shapes can be used, in particular when using multi-columns. The column comprises the nucleic acid binding solid phase. Said solid phase that is comprised in said column should allow the passage of a solution, respectively the sample when applied to the column. This means that if e.g. a centrifuge force is applied to the column, a solution and/or the sample is enabled to pass through the column in direction of the centrifuge force. As discussed above, when using a respective column based nucleic acid isolation procedure, the sample is usually passed through the column, e.g. assisted by centrifugation or vacuum, and the nucleic acids bind to the comprised nucleic acid solid phase during said passage. The column can be used in a single format or in a multi-format. Such multi-columns having a similar format as multi-well plates and which comprise a nucleic acid binding solid phase such as a membrane, are well-known in the prior art. Preferably, the column is a spin column.

As nucleic acid binding solid phase, any solid phase can be used that is usually utilized in column based nucleic acid isolation procedures. Preferably, a nucleic acid binding membrane, and thus a membrane that is capable of binding nucleic acids is used in step a). Suitable membranes include but are not limited to hydrophilic membranes, hydrophobic membranes and membranes which bind nucleic acids via ion exchange. Examples include but are not limited to silica membranes, glass fiber membranes, nylon membranes, cellulose membranes such as nitrocellulose membranes, modified cellulose membranes (e.g. acetyl- or hydroxy-), paper membranes, in particular modified papers. Preferably, the membrane is porous. Furthermore, it is preferred to use a membrane comprising or consisting of silica. A further common nucleic acid binding solid phase comprised in a column is a fill of nucleic acid binding particles, such as silica particles, or a layer of a nucleic acid binding material (e.g. a silica gel). E.g. the silica particles can be arranged as a layer on an inert filter or membrane, thereby forming a nucleic acid binding solid phase. The problems described above with respect to the loss of target nucleic acids and in particular the loss of small target nucleic acids are the more dominant, the thinner the nucleic acid binding solid phase is. This, because a thin layer of a nucleic acid binding solid phase comprised in a column (similar to a nucleic acid binding membrane) increases the risk that released small target nucleic acids can quickly escape and thus get lost during the nucleic acid isolation procedure. As described above, the present invention provides a solution to that problem and thereby allows isolating target nucleic acids including small target nucleic acids with high yield. Thus, according to one embodiment, the nucleic acid binding solid phase comprised in the column has an overall height which is equal to or smaller than its width. E.g. the nucleic acid binding solid phase may be composed of a layer of a nucleic acid binding material and/or a fill, respectively layer of nucleic acid binding particles, preferably silica particles, which is applied as a small layer onto a membrane or filter. Suitable nucleic acid binding materials and particles are described in detail below.

To alleviate the passage of the sample through the nucleic acid binding solid phase comprised in the column, suitable means can be used such as e.g. centrifugation or the use of a pressure difference-generating apparatus which e.g. presses the sample through the column, respectively the nucleic acid binding solid phase or sucks it through the nucleic acid binding solid phase by applying a vacuum. Respective means are well known in the prior art and thus need no further description here.

As nucleic acid binding solid phase which may be used in step d), any material that is capable of binding nucleic acids and in particular small target nucleic acids can be used and include a variety of materials that are capable of binding nucleic acids under suitable conditions. Said solid phase used in step d) does not need to be column based, even though this is preferred for the ease of handling. Exemplary solid phases that can be used in conjunction with the present invention include, but are not limited to, compounds comprising silica, including but not limited to, silica particles, silicon dioxide, diatomaceous earth, glass, alkylsilica, aluminum silicate, and borosilicate; nitrocellulose; diazotized paper; hydroxyapatite (also referred to as hydroxyl apatite); nylon; metal oxides; zirconia; alumina; polymeric supports, diethylaminoethyl- and triethylaminoethyl-derivatized supports, hydrophobic chromatography resins (such as phenyl- or octyl Sepharose) and the like. The term solid phase is not intended to imply any limitation regarding its form or design. Thus, the term solid phase encompasses appropriate materials that are porous or non-porous; permeable or impermeable; including but not limited to membranes, filters, sheets, particles, magnetic particles, beads, gels, powders, fibers, and the like. According to one embodiment, the surface of the solid phase such as e.g. the silica solid phase used in step d) or the nucleic acid binding solid phase used in step a) is not modified and is, e.g., not modified with functional groups. As described above, it is preferred that a nucleic acid binding membrane is used in step d). Said membrane may have the same characteristics described above for the nucleic acid binding membrane that is used in step a). It is in particular preferred though that the same nucleic acid binding membrane that was used in step a) is used for re-binding the "escaped" small target nucleic acids to said membrane in step d).

It is also within the scope of the present invention to perform additional intermediate steps than the ones described herein. However, according to certain embodiments, no additional steps other than the ones described herein are performed.

Furthermore, the present invention pertains to the use of a recovery solution capable of binding small nucleic acids to a membrane, for re-binding collected small nucleic acids that were released from said nucleic acid binding membrane during an on-membrane treatment. As discussed above, the nucleic acids are preferably collected as flow-through in order to ensure that small nucleic acids that e.g. slipped under the membrane are also efficiently collected and thus recovered. Details of the recovery solution and the conditions that result in the release of the small target nucleic acids are described above, it is referred to the above disclosure.

Furthermore, the present invention pertains to a kit for performing the methods according to the present invention which comprises:

a) a nucleic acid binding solid phase, preferably a membrane, comprised in a column;
b) a binding buffer for binding a target nucleic acid including small target nucleic acids to said nucleic acid binding solid phase, comprising a chaotropic agent and an alcohol;
c) a recovery solution comprising a chaotropic agent in a concentration of 0.1M up to the saturation limit, preferably 0.5M up to the saturation limit and/or an alcohol in a concentration of at least 50%; and
d) instructions for performing the method according to the present invention.

Details of the recovery solution, the nucleic acid binding solid phase, which preferably is a membrane and the binding buffer as well as the associated advantages are described above, it is referred to the above disclosure.

EXAMPLES

Example 1

Isolation of Small Nucleic Acids According to the Present Invention or the Reference Method FFPE samples from rat kidney (the samples were stored after fixation and embedding for two month at room temperature) and FFPE samples derived from rat lung (the samples were stored after fixation and embedding for 27 months at room temperature) were used. Slices having a size of 10 µm thickness were obtained by using a Microtom. One slice was used per sample. All samples were processed twice. For the subsequent isolation of RNA from the obtained FFPE slices, components of the RNeasy FFPE kit (QIAGEN) and the QIAamp FFPE kit (QIAGEN) were used.

In order to remove the paraffin from the samples, the samples were incubated for one hour in 1 ml heptane. 50 µl methanol was added, mixed, the sample was centrifuged, the supernatant was collected and the sample was dried for 5 minutes at room temperature.

This respectively derived de-paraffinized sample pellets were mixed with 150 µl of a proteinase K digestion buffer (buffer PKD, QIAGEN) and furthermore, were mixed with 10 µl of a proteinase K solution (>600 mAU/ml). The mixture was incubated for 15 minutes at 56° C. under shaking at 1400 rpm. The samples were cooled on ice for 3 minutes and centrifuged for 30 minutes for removing unsolved components. The DNA containing pellet was discarded (said DNA containing pellet can optionally be used for isolating the DNA if desired) and the supernatant was collected for isolating the contained RNA as target nucleic acid. In order to exclude variations attributable to the used sample materials, the collected supernatants were combined, mixed and divided into aliquots of 150 µl.

Subsequently, these aliquots were incubated for 15 minutes at 80° C. for removing cross-links in the RNA (resulting from the FFPE preservation). Afterwards, 300 µl of an chaotropic lysis buffer (buffer RLT, QIAGEN) was added, and the resulting mixture was mixed with 1050 µl ethanol. The resulting mixture was applied to a silica membrane (RNeasy MinElute Column, QIAGEN) and passed through the membrane by centrifugation for 15 seconds at 10.000 rpm. The membrane to which the target nucleic acids were bound, was washed by passing a washing buffer containing a chaotrop agent and ethanol containing (RWT, QIAGEN) through the membrane. Afterwards, 80 µl of a mixture comprising 10 µl DNAse 1 and 70 µl of a DNAse reaction buffer (buffer RDD, QIAGEN) was applied to the membrane and incubated for 15 minutes at room temperature in order to remove remaining genomic DNA.

For isolating the RNA according to the reference method as it is known in the prior art, a washing buffer, comprising a chaotropic agent and ethanol (buffer RWT, QIAGEN) was added again after performing the on-membrane DNAse digest to remove the DNase reaction solution. The washing buffer RWT enhances due to the comprised chaotropic agent and the alcohol the binding of the RNA to the membrane. Afterwards, the membrane was washed by adding twice 500 µl of an alcohol containing washing buffer (RPE, QIAGEN) and passage through the membrane. The membrane was dried by centrifugation for 5 minutes at 14.000 rpm. The RNA was eluted by centrifugation after applying 30 µl water and performing an incubation step for 1 minute.

For isolating the RNA according to the method of the present invention, a recovery solution containing between 1 and 1.5M GTC, 75% isopropanol, sodium citrate, pH 7 was applied to and passed through the membrane by centrifugation after performing the on-membrane DNase digest. The flow-through was collected and re-applied and passed through the membrane by centrifugation. Thereby, in particular small target nucleic acids that were released from the membrane during the on-membrane DNase digest are again bound to the membrane and are thus recovered. Afterwards, the membrane was washed by adding twice 500 µl of an alcohol containing washing buffer (RPE, QIAGEN) and passage through the membrane. The membrane was dried by a centrifugation step for 5 minutes at 14.000 rpm. The RNA was eluted by centrifugation after applying 30 µl water and performing an incubation step for 1 minute.

The size distribution of the RNA isolated from kidney tissue was analysed by using an Agilent Bioanalyzer to demonstrate the improvements achieved with the method according to the present invention. The same amount of RNA (in ng) was applied (determined by a OD measurement). The results are shown in FIG. 1, wherein "+" characterizes the RNA that was isolated using the method according to the present invention and wherein "−" characterizes the RNA that was isolated using the reference method. As can be seen, performing the essential collection and reapplications steps c) and d) according to the method of the present invention results in a considerable increase of small target RNAs in the isolated RNA. This can be derived from the considerably darker bands in the range of small RNAs that can be detected in the RNA that was isolated according to method of the present invention (these bands are marked by the arrow in FIG. 1). Thus, the amount of small RNA was considerably increased in the RNA isolated with the method according to the present invention compared to the reference method. The RNA isolated with the reference method only comprised a low amount of small RNA and accordingly, more large RNA molecules can be detected in the applied amount of RNA. Therefore, this example shows that the method according to the present invention considerably increases the yield of small RNAs in the isolated RNA. For the avoidance of doubt it is emphasised that the total amount of larger RNA molecules is basically identical when performing the method according to the present invention or the reference method, as was confirmed by RT-PCRs detecting amplicons of larger mRNAs.

The isolated RNA was also analysed by using quantitative real-time-RT-PCR in order to analyse the advantageous effects of the method according to the present invention on the yield of specific small RNAs.

For this purpose, the isolated RNA was used for determining an amplicon of the micro-RNAs miR29a and miR30b using the ABI TaqMan® MicroRNA assay (Applied Biosystems) according to the manufacture's instructions. 20 ng RNA were used in the reversed transcription reaction by using the TaqMan® MicroRNA reverse transcription kit and the corresponding primers has-miR30a and has-miR29b (Applied Biosystems) according to the manufacturer's instructions. The amplification of the miRNA amplicons using the above mentioned systems was performed by using 2 µl of cDNA (dilution 1:20) in a real-time amplification system (ABI PRISM 7900HT Sequence Detection System, Company ABI). The mean values (derived from duplicates) of the measured ct-values were determined and are summarised in table 1.

TABLE 1 miRNA-detection performing the RNA isolation according to the present invention or the reference method

| | | miR29a | miR30b |
|---|---|---|---|
| Kidney | with rebinding | 24.45 | 24.14 |
| | without rebinding | 26.61 | 26.06 |
| Lung | with rebinding | 24.5 | 25.08 |
| | without rebinding | 26.52 | 26.83 |

The results show that using the method according to the present invention results in ct-values which are considerably lower than the ct-values obtained from the corresponding samples obtained by the reference method. The lower ct-values achieved with the method according to the present invention are attributable to the fact that the respectively isolated RNA comprises larger amounts of the detected miRNAs. This shows that the RNA isolated according to the method of the present invention comprises more small nucleic acids than the RNA isolated with the reference method. The method according to the present invention considerably improves the isolation of small nucleic acids from biological samples because the yield of small target nucleic acids is increased. As is shown by the reference example, the simple addition of a washing buffer comprising a chaotropic agent and ethanol which enhances the binding of potentially released target nucleic acids to the membrane (as is done in the prior art) is not sufficient for efficiently re-capturing the small target nucleic acids. As is discussed above, this is most likely due to the fact that released small target nucleic acids escape from the nucleic acid binding surface of the membrane and therefore, can not be re-captured by the methods according to the prior art.

Example 2

Use of Different Concentrations of Chaotropic Agents in the Recovery Solution

In this example FFPE samples of rat kidney were used. The FFPE samples were stored after fixation and embedding for approximately two months at room temperature. Slices of 10 µm thickness were obtained from said FFPE samples by using a Microtom. One slice was used per sample. All samples were processed twice. For the subsequent isolation of RNA from the respective FFPE slices, components of the RNeasy FFPE kit (QIAGEN) and the QIAamp FFPE kit (QIAGEN) was used.

The isolation of RNA according to the method of the present invention and the reference method were done as is described in example 1. For rebinding "escaped" small RNAs after performing the on-membrane DNAse digest, three different compositions were used as recovery solution. The tested recovery solutions comprised 70% ethanol, sodium citrate, pH 7 and

A) 1.16 M GTC

B) 1.5 M GTC

C) 1.8 M GTC.

Figure 2:
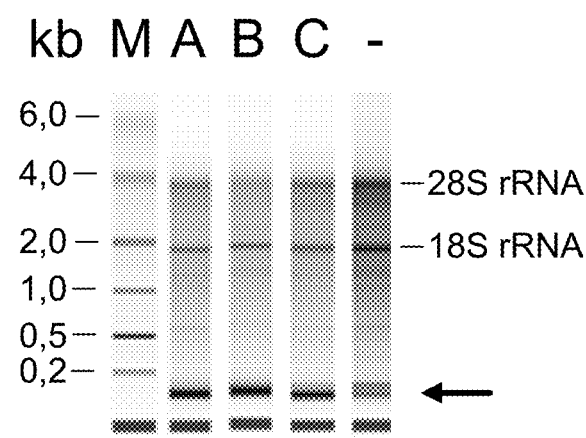

The size distribution of the RNA isolated from the kidney sample was analysed using an Agilent Bioanalyzer. Similar to the result shown in FIG. 1 it was again found, that the proportion of small RNAs in the total RNA isolated with the reference method is considerably lower than in the RNA isolated with the method according to the present invention. Therefore, the RNA isolated according to the method of the present invention comprised small RNAs with higher yield. As is also demonstrated by FIG. 2, all tested recovery solutions A) to C) were suitable for efficiently re-capturing the small target nucleic acids wherein the reference method "−" only yielded low amounts of small RNA.

In order to analyse the effect of the different tested recovery solutions on the isolation of the small RNAs, the RNA was analysed by performing a quantitative real-time-RT-PCR as is described in example 1. For this purpose, the isolated RNA was used for detecting an amplicon of the micro RNAs miR29a and miR16 using the ABI TaqMan® MicroRNA assay (Applied Biosystems) according to the manufacturer's instructions.

The mean values of the measured ct-values (derived from the duplicates) were determined and are summarised in table 2.

TABLE 2 miRNA detection after RNA isolation using the method according
to the present invention or the reference method

|  | Composition | miR16 | miR29a |
|---|---|---|---|
| without rebinding | — | 28.56 | 27.78 |
| with rebinding | A | 26.46 | 26.06 |
| with rebinding | B | 25.64 | 25.60 |
| with rebinding | C | 26.71 | 25.90 |

The results show, that the ct-values are considerably lower when using the RNA isolated according to the method of the present invention compared to the RNA isolated by the reference method. This is due to the fact that the method according to the present invention considerably increases the yield of small RNAs in the isolated RNA. As is shown by the results, different concentrations of chaotropic agents can be successfully used in the recovery solution.

Example 3

Suitability of Different Alcohols and Different Alcohol Concentrations in the Recovery Solution In this example, FFPE samples from rat kidney (the samples were stored after fixation and embedding for two months at room temperature) and from rat lung (the samples were stored after fixation for approximately 27 months at room temperature) were used. Slices having a thickness of 10 μm were obtained by using a Microtom; one slice was used per sample. All samples were processed twice. For the subsequent isolation of RNA from the FFPE slices, components of the RNeasy FFPE kit (QIAGEN) and the QIAamp FFPE kit (QIAGEN) were used.

The isolation of RNA using the method according to the present invention or the reference method was performed as is described in example 1. For capturing the "escaped" small RNA after performing the on-membrane DNAse treatment, recovery solutions having four different compositions were tested. The recovery solutions comprised 1.5 M GTC, sodium citrate, pH 7 and A) 70% ethanol
B) 75% ethanol
C) 70% isopropanol
D) 75% isopropanol.

Figure 3:
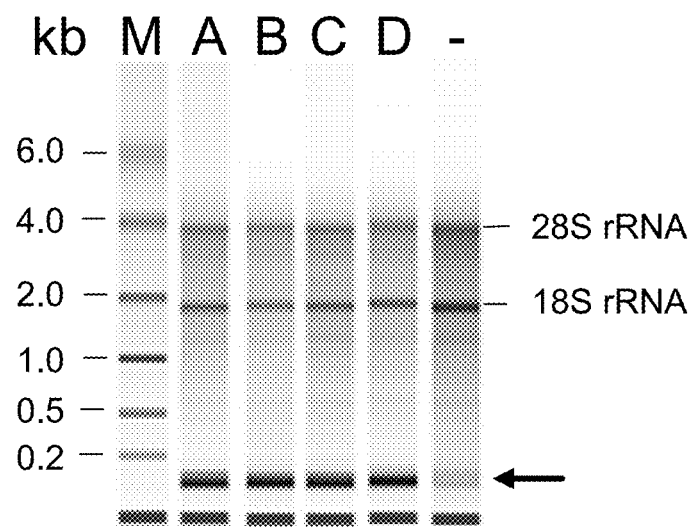

The size distribution of the RNA isolated from kidney tissue was analysed using an Agilent Bioanalyzer. Similar to the results shown in FIG. 1 and FIG. 2 it was found (see FIG. 3), that the portion of small RNAs is considerably increased in the isolated total RNA when using the method according to the present invention. All tested recovery solutions were basically equally effective for efficiently re-capturing small RNAs wherein the reference method "–" only yielded low amounts of small RNA.

In order to analyse the effect of the different recovery solutions on the isolation of specific small RNAs, the isolated RNA was analysed using the quantitative real-time-RT-PCR methods described in example 1. The isolated RNA was used for determining the amplicon of the micro-RNAs miR29a by using the ABI TaqMan® MicroRNA assay (Applied Biosystems) according to the manufacturer's instructions.

The mean values of the measured ct-values (derived from the duplicates) were determined and are summarised in table 3.

TABLE 3 miR29a detection after RNA isolation using the method according
to the present invention or the reference method

|  | Composition | Kidney | Lung |
|---|---|---|---|
| without rebinding | — | 26.61 | 26.42 |
| with rebinding | A | 25.41 | 25.40 |
| with rebinding | B | 24.66 | 25.15 |
| with rebinding | C | 24.74 | 25.22 |
| With rebinding | D | 24.45 | 24.50 |

Again, the results show that using the method according to the present invention considerably increases the yield of small RNAs in the isolated RNA as can be derived from the lower ct-values. Different alcohols and alcohol concentrations can be used in the recovery solution.

Example 4

Isolation of Small Nucleic Acids According to the Present Invention or the Reference Method from Non-Fixed Samples Tissue samples of rat lung (the samples were stored after resection in RNAlater at −80° C.) were used for RNA isolation using a lysis buffer comprising a chaotropic agent. All samples were processed twice. For the subsequent isolation of RNA, components of the RNeasy kit (QIAGEN) and miRNeasy kit (QIAGEN) were used.

Phenol-Chloroform Based Lysis

Each 10 mg of rat lung was homogenized in 700 μl of a phenol-based lysis buffer (buffer QIAzol, QIAGEN) with one 5 mm steal bead for 5 min at 25 Hz using a beadmill (TissueLyzer, QIAGEN). Afterwards, the samples were incubated for 5 min at room temperature prior to adding 140 μl chloroform. After 2 minutes incubation at room temperature the lysates were centrifuged for 15 min at 12000×g at 4° C. The upper phase was removed and mixed with 525 μl ethanol. The resulting mixture was applied to a silica membrane (RNeasy Mini Column, QIAGEN) and passed through the membrane by centrifugation for 15 seconds at 13.000 rpm. The membrane to which the target nucleic acids were bound, was washed by passing a washing buffer containing a chaotropic agent and ethanol (RWT, QIAGEN) through the membrane.

Chaotropic Agent Based Lysis

Each 10 mg of rat lung were homogenized in 350 μl of a lysis buffer (buffer RLT including β mercaptoethanol, QIAGEN) with one 5 mm steal bead for 5 min at 25 Hz using a beadmill (TissueLyzer, QIAGEN). Afterwards, the samples were centrifuged for 4 min at 14000 rpm and the supernatant was mixed with 525 μl ethanol. The resulting mixture was applied to a silica membrane (RNeasy Mini Column, QIAGEN) and passed through the membrane by centrifugation for 15 seconds at 10.000 rpm.

The membrane to which the target nucleic acids were bound, was washed by passing a washing buffer containing a chaotropic agent and ethanol (RWT, QIAGEN) through the membrane.

Further Processing of All Samples

80 μl of a mixture comprising 10 μl DNAse 1 and 70 μl of a DNAse reaction buffer (buffer RDD, QIAGEN) was applied to the membrane and incubated for 15 minutes at room temperature in order to remove remaining genomic DNA.

For isolating the RNA according to the reference method or according to the method of the present invention, all further steps were done as described in example 1. The RNA was eluted twice by centrifugation after applying 50 μl water (phenol-based lysis) or 40 μl water (chaotropic agent based lysis) and performing an incubation step for 1 minute.

Analysis of the Eluates

The isolated RNA was analysed using the quantitative real-time-RT-PCR methods described in example 1. The isolated RNA was used for determining the amplicon of the micro-RNAs miR29a by using the ABI TaqMan® MicroRNA assay (Applied Biosystems) according to the manufacturer's instructions.

The mean values of the measured ct-values (derived from the duplicates) were determined and are summarised in table 4.

TABLE 4 miR29a detection after RNA isolation using the method according to the present invention or the reference method from non-fixed samples

| | Lysis | ct value |
|---|---|---|
| without rebinding | phenol based lysis | 23.36 |
| with rebinding | phenol based lysis | 22.16 |
| without rebinding | Chaotropic agent based lysis | 26.38 |
| with rebinding | Chaotropic agent based lysis | 23.69 |

Again, the results show that using the method according to the present invention considerably increases the yield of small RNAs in the isolated RNA, also in non-fixed samples, as can be derived from the lower ct-values.

Example 5

Isolation of Small DNA Using the Method According to the Present Invention

As DNA samples, a 10 bp DNA-ladder and a 50 bp DNA-ladder were used. For the subsequent isolation, components of the QIAamp MinElute Kits (QIAGEN) were used. 2 μg of the 10 bp DNA-ladder and 5 μg of the 50 bp DNA-ladder were mixed with 180 μl lysis buffer (buffer ATL, QIAGEN). The DNA was purified from said mixture using the reference method (either with or without an on-membrane treatment of the DNA) or the method according to the present invention.

For the reference method without an on-membrane treatment (sample (a)), the lysis-DNA mixture was mixed with 4 μl RNA (100 mg/ml) and incubated for 2 min at room temperature. Subsequently, 200 μl of a binding buffer comprising a chaotropic agent (buffer AL, QIAGEN) and 200 μl ethanol was added. The resulting mixture was applied to and passed through a silica membrane (QIAamp MinElute column, QIAGEN) by centrifugation (1 min, 8000 rpm). The membrane was washed by passing 500 μl of an alcohol and chaotropic agent containing wash buffer (AW1, QIAGEN) and 500 μl of an alcohol containing wash buffer (AW2) through the membrane. The membrane was dried by centrifugation (1 min, 14000 rpm). The DNA was eluted by centrifugation after applying an elution buffer (30 μl, ATE, QIAGEN) and incubation for 1 min.

In the reference method wherein an on-membrane treatment of the DNA was performed (samples b, c, e, f) and in the method according to the present invention (samples d, g), the mixtures comprising the lysis buffer and the DNA sample were mixed with 200 μl of a binding buffer comprising a chaotropic agent (buffer AL, QIAGEN) and 200 μl ethanol. The resulting mixture was applied to and passed through a silica membrane (QIAamp MinElute column, QIAGEN) by centrifugation (1 min, 8000 rpm).

Afterwards, different on-membrane treatments were performed, while the DNA was bound to the membrane. Some samples were treated with RNase (samples b, c, d) the others were treated with a protease (samples e, f, g).

For performing the on-membrane RNase treatment, 80 μl of an RNase mixture, consisting of 4 μl RNase A (100 mg/ml) and 76 μl of an RNase reaction buffer (buffer RDD, QIAGEN) was applied to the membrane and incubated for 5 min at room temperature.

For performing the on-membrane protease treatment, 80 μl of a protease mixture consisting of 20 μl proteinase K (>600 mAU/ml) and 60 μl of a protease reaction buffer (buffer RDD, QIAGEN) was applied to the membrane and incubated for 15 min at 56° C.

For the samples processed according to the reference method (samples b, c, e, f), 500 μl of a buffer comprising a chaotropic agent and ethanol (buffer AW1, QIAGEN (samples b, e) or buffer RWT, QIAGEN (samples c, f)) and 500 μl of an alcohol containing wash buffer AW2 (QIAGEN) were passed through the membrane. The membrane was dried by centrifugation (1 min, 14000 rpm). The DNA was eluted by centrifugation after applying an elution buffer (30 μl, ATE, QIAGEN) and incubation for 1 min.

For the samples processed according to the method according to the present invention (samples d and g), a recovery solution (comprising 1 to 1.5M GTC, 75% isopropanol, sodium citrate pH 7) was applied to and passed through the membrane by centrifugation.

The flow-through was reapplied to and passed through the membrane by centrifugation in order to re-bind escaped small DNA molecules. Afterwards, the membrane was washed by passing 500 μl of an alcohol containing wash buffer (AW2) through the membrane. The membrane was dried by centrifugation (1 min, 14000 rpm). The DNA was eluted by centrifugation after applying an elution buffer (30 μl ATE, QIAGEN) and incubation for 1 min.

The yield of the DNA isolated by the different methods tested in example 5 was determined at 260 nm. Table 5 shows the mean values of the duplicates.

TABLE 5

DNA yield after DNA isolation using the method according to the present invention or reference methods with and without on membrane treatment of the DNA

| DNA | sample | DNA isolation method | on membrane treatment | yield (μg) |
|---|---|---|---|---|
| 10bp ladder | a | Reference | — | 0.55 |
| | b | Reference | RNase | 0.08 |
| | c | Reference | RNAse | 0.11 |
| | d | according to invention | RNAse | 0.67 |
| | e | Reference | proteinase | 0.28 |
| | f | Reference | proteinase | 0.27 |
| | g | according to invention | proteinase | 0.8 |
| 50bp ladder | a | Reference | — | 4.26 |
| | b | Reference | RNase | 0.66 |
| | c | Reference | RNAse | 0.63 |
| | d | according to invention | RNAse | 3.58 |
| | e | Reference | proteinase | 1.00 |
| | f | Reference | proteinase | 0.54 |
| | g | according to invention | proteinase | 3.07 |

As is demonstrated by table 5, the method according to the present invention considerably increases the yield of small DNA in nucleic acid isolation methods wherein an on-membrane treatment is performed.

Example 6

Suitability of Different Chaotropic Agents and Different Buffer Agents in the Recovery Solution Tissue samples of rat lung (the samples were stored after resection in RNAlater at −80° C.) were used for RNA isolation using a lysis buffer comprising a chaotropic agent. For the subsequent isolation of RNA, components of the RNeasy kit (QIAGEN) and miRNeasy kit (QIAGEN) were used.

In order to provide homogeneous starting material for comparison of different recovery solutions, a pool lysate was prepared from rat lung tissue. 350 µl of a lysis buffer (buffer RLT including β-mercaptoethanol, QIAGEN) were added for each 10 mg of tissue, and the material was homogenized using a rotor stator homogenizer. After homogenization the pool lysate was separated into aliquots of 350 µl lysate and used for all subsequent RNA purifications. The lysate was mixed with 525 µl 96-100% ethanol, applied to a silica membrane (RNeasy Mini Column, QIAGEN) and passed through the membrane by centrifugation for 15 seconds at 10.000 rpm.

As a reference without rebinding (see ref in FIG. 4), the membrane to which the target nucleic acids were bound was washed by passing a washing buffer containing a chaotropic agent and ethanol (RWT, QIAGEN) through the membrane. 80 µl of a mixture comprising 10 µl DNAse 1 and 70 µl of a DNAse reaction buffer (buffer RDD, QIAGEN) was applied to the membrane and incubated for 15 minutes at room temperature in order to remove remaining genomic DNA. Then the membrane was again washed by passing a washing buffer containing a chaotropic agent and ethanol (RWT, QIAGEN) through the membrane. Afterwards, the membrane was washed by adding twice 500 µl of an alcohol containing washing buffer (RPE, QIAGEN) and passage through the membrane. The membrane was dried by centrifugation for 3 minutes at 14.000 rpm. The RNA was eluted twice by centrifugation after applying 40 µl water and performing an incubation step for 1 minute.

For isolating the RNA according to the method of the present invention, the membrane to which the target nucleic acids were bound, was washed by passing a recovery solution containing a chaotropic agent, a buffer component and isopropanol in different compositions (table 6) through the membrane. The flow-through was discarded. 80 µl of a mixture comprising 10 µl DNAse 1 and 70 µl of a DNAse reaction buffer (buffer RDD, QIAGEN) was applied to the membrane and incubated for 15 minutes at room temperature in order to remove remaining genomic DNA. After performing the on-column DNAse digestion step, recovery solution of the same type was applied to and passed through the membrane by centrifugation. The flow-through was collected, re-applied and passed through the membrane by centrifugation. Thereby, in particular small target nucleic acids that were released from the membrane during the on-membrane DNase digest are again bound to the membrane and are thus recovered. Afterwards, the RNA was eluted from the membrane as described above for the reference method. (All samples were processed twice.)

TABLE 6

Composition of different recovery solutions

| recovery solution | chaotropic agent | buffer component | isopropanol |
|---|---|---|---|
| A | 1.25M guanidinium isothiocyanate | 6.25 mM sodium citrate pH 7 | 75% |
| B | 1.25M guanidinium isothiocyanate | 6.25 mM Tris pH 7 | 75% |
| C | 1.25M guanidinium isothiocyanate | 6.25 mM MOPS pH 7 | 75% |
| D | 1.25M guanidinium isothiocyanate | 6.25 mM MES pH 7 | 75% |
| E | 1.75M guanidinium hydrochloride | 6.25 mM MOPS pH 7 | 75% |
| F | 1.25M guanidinium hydrochloride | 6.25 mM MOPS pH 7 | 75% |
| G | 0.2M sodium flouroacetate | 20 mM Tris pH 8 | 80% |
| H | 0.2M sodium perchlorate | 20 mM Tris pH 8 | 80% |

The isolated RNA was analysed using the quantitative real-time-RT-PCR methods described in example 1. The isolated RNA was used for determining the amplicon of the micro-RNA miR16 by using the miScript System (QIAGEN) according to the manufacturer's instructions.

Figure 4:
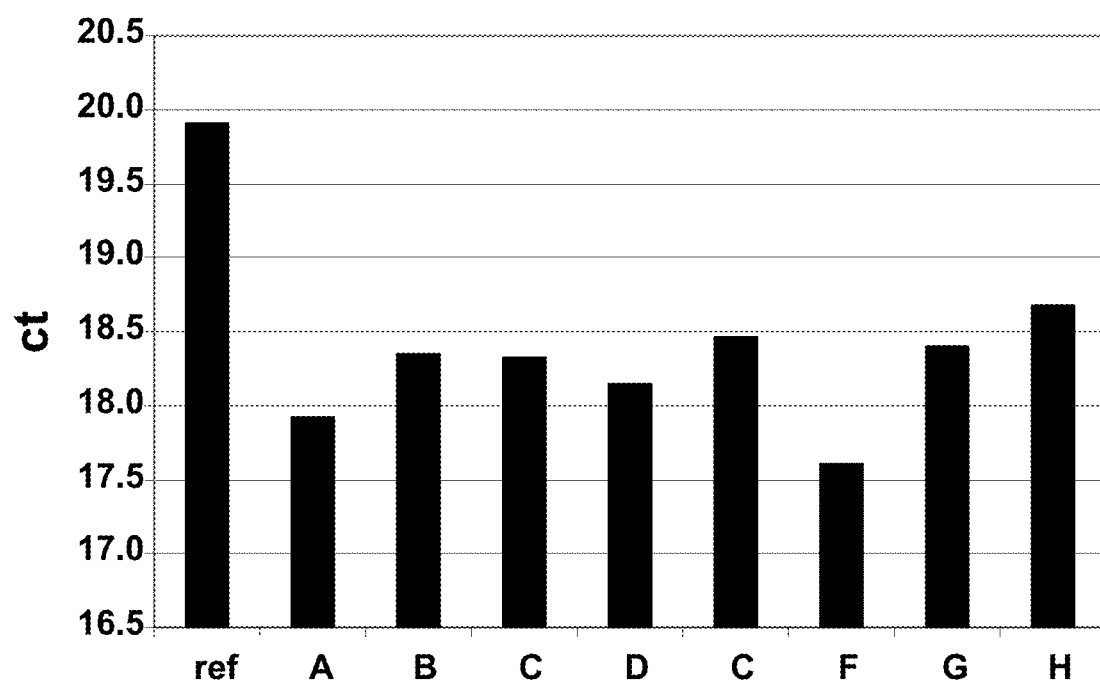
FIG. 4 shows the results of a miR16 detection assay after RNA isolation performing the method according to the present invention using different recovery solutions or the reference method, wherein no respective recovery solution is used. As can be seen, the Ct values are considerately reduced with the recovery solutions according to the present invention, thereby demonstrating the improved isolation of small RNA.

The mean values of the measured ct-values (derived from the duplicates) were determined and are shown in FIG. 4. Again, the results show that using the method according to the present invention considerably increases the yield of small RNAs in the isolated RNA as can be derived from the lower ct-values. Different chaotropic agents and different buffer components can be used in the recovery solution.

Example 7

Isolation of RNA and DNA Using the Method of the Present Invention or Using Methods Based on Prior Art Protocols FFPE samples derived from rat liver (the samples were stored after fixation and paraffin embedding for approx. 2 months at room temperature), from rat kidney (stored and embedded correspondingly for approx. 19 months) and from rat lung (stored and embedded correspondingly for approx. 8 months) were used. Tissue slices having a size of 10 µm thickness were obtained by applying a microtome. Two slices were used per sample. All samples were processed in triplicats. For subsequent isolation of RNA and DNA, components of the kit RNeasy FFPE (QIAGEN) and the kit Allprep DNA RNA FFPE (QIAGEN) were employed using the method of the present invention.

Alternatively, methods based on prior art kit protocols were used for comparison. The following kits from different providers were used:

FFPE RNA/DNA Purification Kit (NORGEN)
RecoverAll™ Total Nucleic Acid Isolation Kit Optimized for FFPE Samples (Ambion)
QuickExtract™ FFPE RNA Extraction Kit (EPICENTRE)
RNA and DNA Isolation from FFPE Samples (Macherey-Nagel)

Method According to the Present Invention

In order to remove the paraffin from the samples, the samples were mixed by vortexing for 10 sec with 1 ml of xylol and centrifuged (2 min 20.000 rpm). The supernatant was completely removed. Then the sample was supplemented with 1 ml of 96% ethanol, mixed by vortexing for 10 sec and centrifuged as above. The supernatant was completely removed, and the sample pellet was dried for 10 minutes at 37° C.

These de-paraffinized sample pellets were mixed with 150 µl of a proteinase K digestion buffer (buffer PKD, QIAGEN) and, 10 µl of a proteinase K solution (>600 mAU/ml). The mixture was incubated for 15 minutes at 56° C. with constant shaking at 450 rpm. The samples were cooled on ice for 3 minutes and centrifuged for 15 minutes at 20.000 g at room temperature. The DNA containing pellet was used for isolating the DNA and the supernatant was collected for isolating the contained RNA.

Subsequently, these RNA containing supernatants were incubated for 15 minutes at 80° C. at 450 rpm on a thermomixer. Afterwards, in each case 320 µl of a chaotropic lysis buffer (buffer RLT, QIAGEN) was added, and the resulting mixture was supplied with 1120 µl 96% ethanol. Reagents were mixed by pipeting and 700 µl were applied to a silica membrane (RNeasy MinElute Column, QIAGEN). The sample was passed through the membrane by centrifugation for 15 seconds at 10.000 rpm and the flow-through was discarded. The remainder of the sample was applied to the membrane accordingly. The membrane to which the target nucleic acids were bound, was washed by passing 350 µl of a recovery solution, consisting of one part 5 M GTC (+25 mM Na citrate) and three parts of isopropanol, (called recovery solution below) through the membrane (15 sec centrifugation at 10.000 rpm). Afterwards, a mixture comprising 10 µl DNAse 1 and 70 µl of a DNAse reaction buffer (buffer RDD, QIAGEN) was applied to the membrane and incubated for 15 minutes at room temperature.

After performing this on-membrane DNase digest, 500 µl of the recovery solution were applied to and passed through the membrane by centrifugation (15 sec 10.000 rpm). The flow-through was collected, re-applied to and passed through the membrane by centrifugation as described above. Thereby, in particular small target nucleic acids that were released from the membrane during the on-membrane DNase digest were rebound to the membrane and thus recovered. Subsequently, the membrane was washed twice by adding 500 µl of an alcohol containing washing buffer (RPE, QIAGEN) and passage through the membrane by centrifugation as above. The membrane was dried by a centrifugation step for 5 minutes at 14.000 rpm. Total RNA was eluted by centrifugation for 1 min at full speed after applying 30 µl of RNAse free water and incubation for 1 minute.

For DNA isolation, 180 µl of buffer ATL (QIAGEN) and 40 µl of proteinase K were added to the each sample pellet. After vortexing, the samples were incubated for 1 h at 56° C. with constant shaking. Then, the samples were incubated for 2 h at 90° C. without shaking. 4 µl RNase A (100 mg/ml) were added to the mixture, mixed in and incubated for 2 min at room temperature. Samples were supplied with 200 µl of buffer AL (QIAGEN) and mixed. 200 µl of 96% ethanol was added and immediately mixed in. The mixture was applied to a QIAamp MinElute column and centrifuged for 1 min at 8,000 g. The flow-through was discarded. Samples were supplied with 700 µl of buffer AW1 (QIAGEN) and centrifuged for 1 min at 8,000 g. The flow-through was discarded. Samples were supplied with 700 µl of buffer AW2 (QIAGEN) and centrifuged as above. The flow-through was discarded. Samples were supplied with 700 µl of 96% ethanol and centrifuged as above. The flow-through was discarded. For drying of the membrane, columns were centrifuged for 5 min at 14,000 rpm with open lid. 30 µl of buffer ATE (QIAGEN) were pipeted directly onto the membrane of the column followed by incubation at room temperature and centrifugation for 1 min at 8000 g. 30 µl eluates were stored at −20° C. until further proceeding.

Methods Based on Prior Art Protocols

The FFPE RNA/DNA Purification Kit (NORGEN) was used for total RNA and DNA isolation according to the manufacturer's instructions. The samples were incubated with proteinase K for approx. 2 h and 24 h at 50° C. for RNA and DNA respectively—the samples were completely lysed. Only in case of RNA, 10 µl of β-mercaptoethanol were added per ml of binding solution. Additional DNA digestion was performed with 10 units of DNase I (QIAGEN). After applying the DNase in the corresponding incubation buffer to the column and subsequent centrifugation, the flow-through was re-applied and incubated for 15 minutes.

The RecoverAll™ Total Nucleic Acid Isolation Kit Optimized for FFPE Samples (Ambion), QuickExtract™ the FFPE RNA Extraction Kit (EPICENTRE) and the kit RNA and DNA Isolation from FFPE Samples (Macherey-Nagel) were employed for total RNA and DNA isolation—including DNA digestion—according to the manufacturers' instructions.

Afterwards, the nucleic acids isolated with the different protocols were inter alia analysed with respect to quality, quantity, DNA contaminations in the isolated RNA and in particular with respect to the yield of isolated small nucleic acids. The results are shown in FIGS. 5 to 9.

The results show that the method according to the present invention enables the parallel but separate isolation of DNA and RNA from the same sample. Here, the isolation of the RNA and DNA takes approx. 6 h in total. Therefore, it can be performed in one working day. The isolated nucleic acids were of high quality. The DNA contamination in the isolated RNA was much lower compared to the prior art methods and the yield of isolated small RNA was considerably higher.

The Epicentre protocol is very fast (approx. 1:10 h for RNA and DNA in total) and simple. However, the obtained "eluates" were milky, yellowish and turbid. Furthermore, the quality of the isolated RNA was not acceptable and the content of small nucleic acids was very low. The Macherey-Nagel protocol enables the parallel isolation of DNA and RNA from the same sample. However, the isolated RNA was more degraded, resulting in higher real-time-PCR ct-values for the RNAs investigated within this example 7 compared to the method according to the present invention. RNA and DNA isolation takes approx. 8:30 h in total, when using this protocol. The NORGEN protocol is very time-consuming (approx. 5:20 h for RNA and approx. 26 h for DNA in the tested form), resulting from the very long proteinase K digestion step (approx. 2 h and 24 h respectively). Furthermore, the results show that the DNA contamination in the isolated RNA is rather high. Furthermore, the yield of small RNA was considerably lower. The Ambion protocol is very time consuming as the recovery of DNA requires a 16 hours protease digestion step which is conflicting regular laboratory workflows. Furthermore, the DNA contaminations in the isolated RNA were higher than with the method according to the present invention and the content of small RNA was lower.

MicroRNA Analysis

Figure 5:
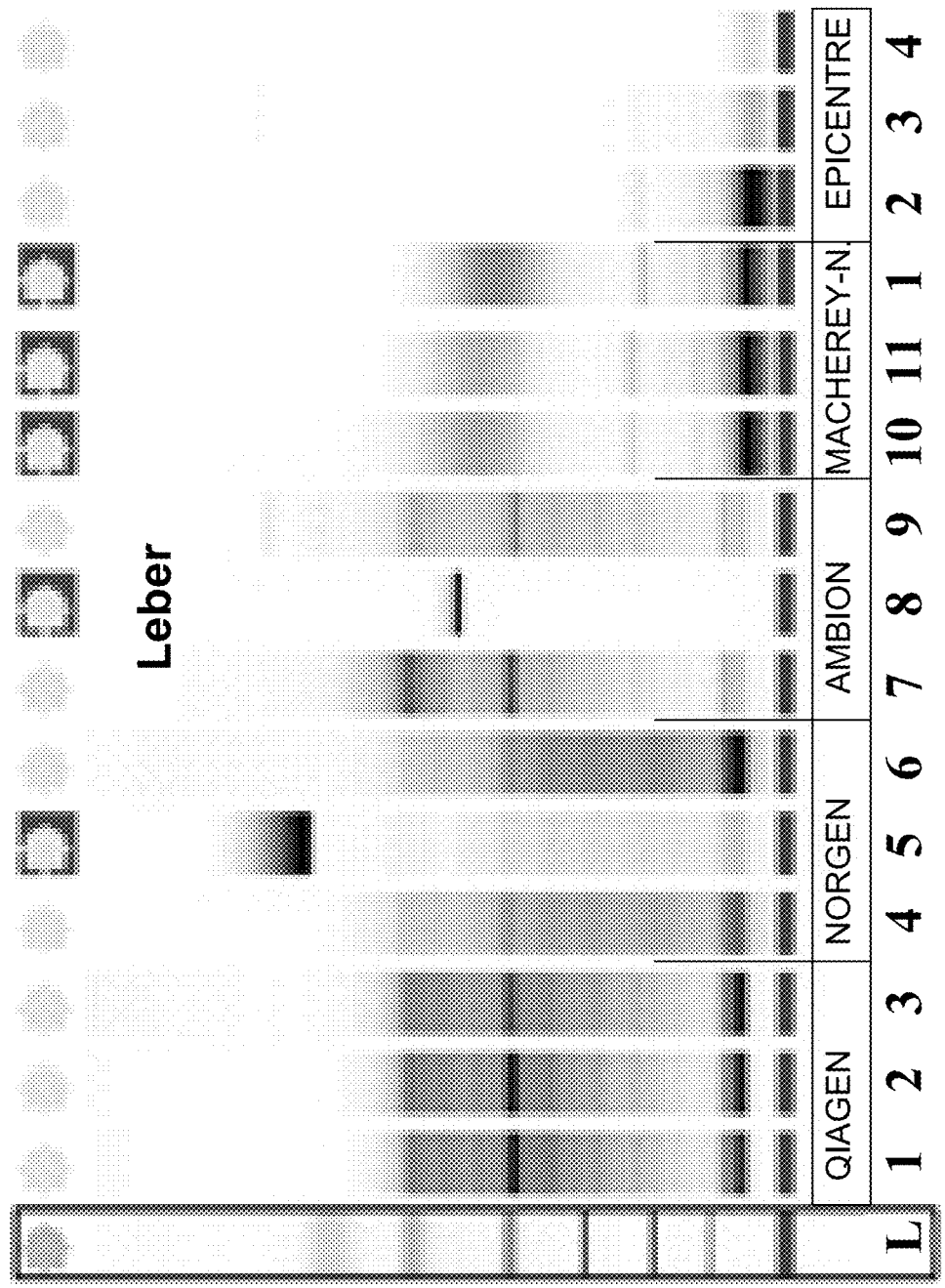
FIG. 5 shows a picture of an agarose gel loaded with RNA purified with 5 different kits (see example 7). The arrow at the right side marks small RNAs.

The size distribution of the RNA isolated from the different tissues was analysed by using an Agilent Bioanalyser to demonstrate the improvements achieved with the method according to the present invention. The same amount of RNA (in ng) was applied (determined by an OD measurement). The results for lung tissue samples (processed in triplicate) are shown in FIG. 5. As can be seen, performing the method according to the present invention in comparison with methods based on kit protocols of the prior art, resulted in both high and reliable yield of small target RNAs in the isolated RNA. This can be derived from the bands in the range of small RNAs. These bands are marked by the arrow in FIG. 5.

Figure 6:
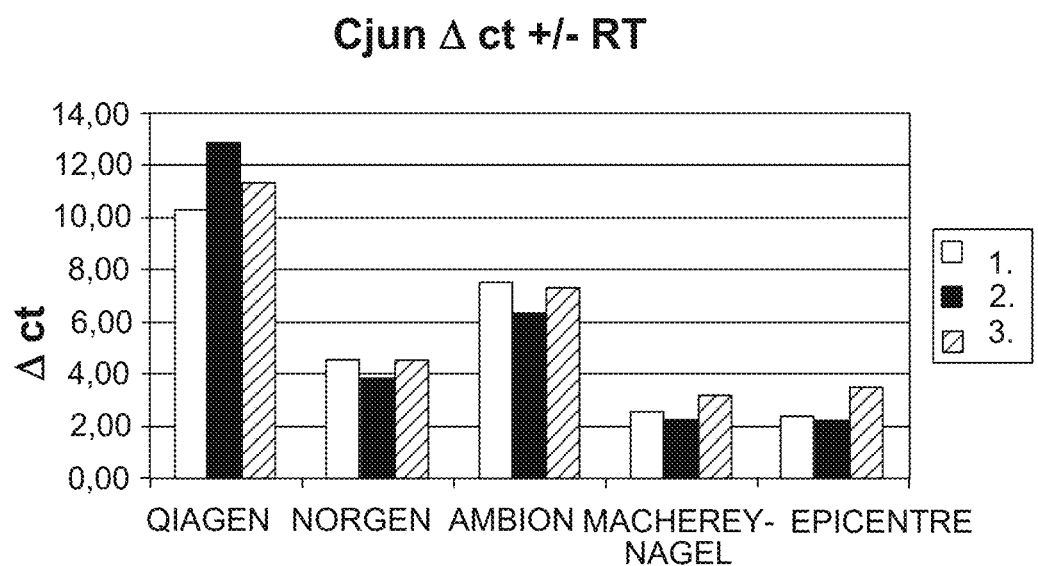
FIG. 6 is a diagram showing the results of a realtime PCR with Cjun mRNA (see example 7). RNA has been purified from FFPE samples derived from 3 different rat tissues: 1. liver (embedded for 2 months), 2. kidney (embedded for 19 months) and 3. lung (embedded for 8 months).

Additionally, it should be emphasized that the method according to the present invention by far resulted in the highest purity of the isolated RNA. FIG. 6 shows the results obtained with cjun mRNA quantified by real-time-PCR with (+) and without (−) reverse transcription (RT) of the isolated RNA respectively. For all the tissues investigated, the obtained differences (delta) in ct-values by far represent the highest values in case of the method according to the present invention (QIAGEN), indicating the lowest contamination with genomic DNA.

Figure 7:
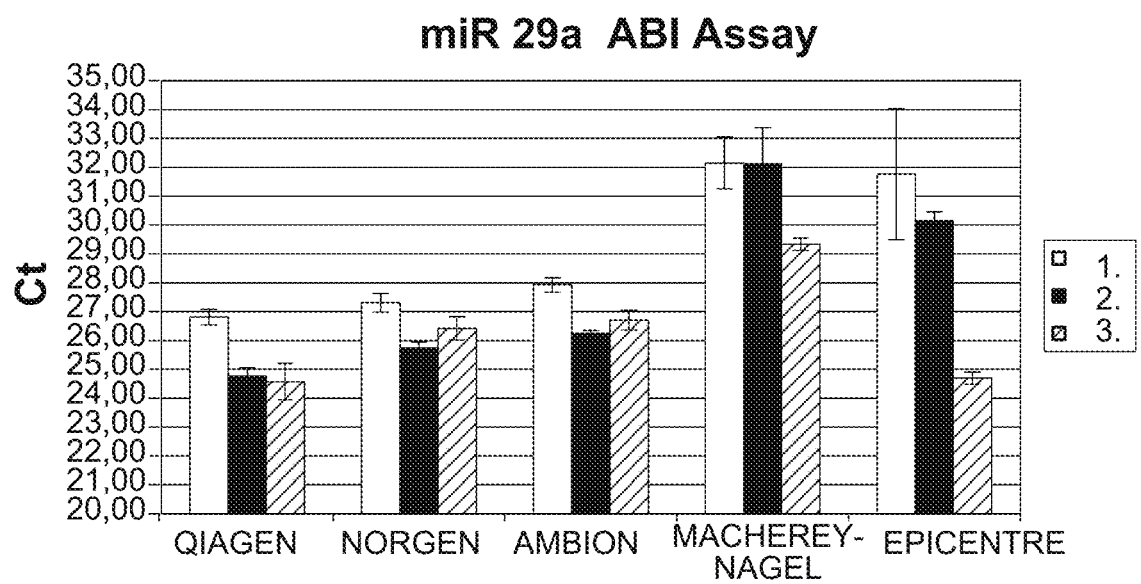
FIG. 7 is a diagram showing the result of a microRNA analysis with miR 29a (see example 7).
Figure 8A:
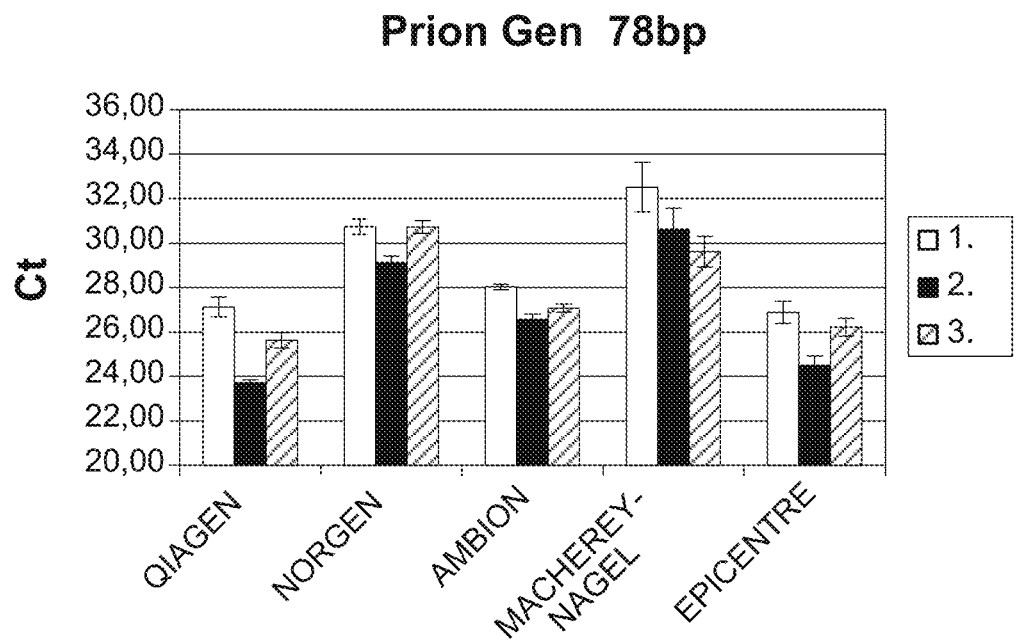
FIG. 8a and FIG. 8b depict the result of a realtime PCR analysis of DNA purified with kits from different suppliers (see example 7). DNA has been purified from FFPE samples derived from 3 different rat tissues: 1. liver (embedded for 2 months), 2. kidney (embedded for 19 months) and 3. lung (embedded for 8 months).
Figure 8B:
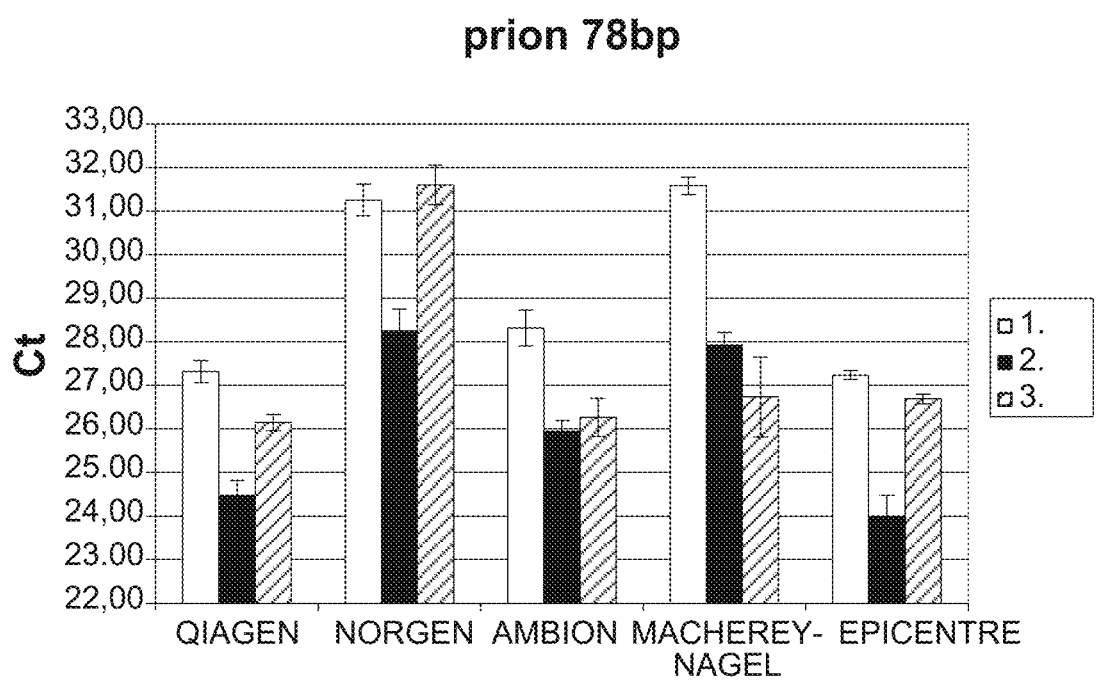
Figure 9A:
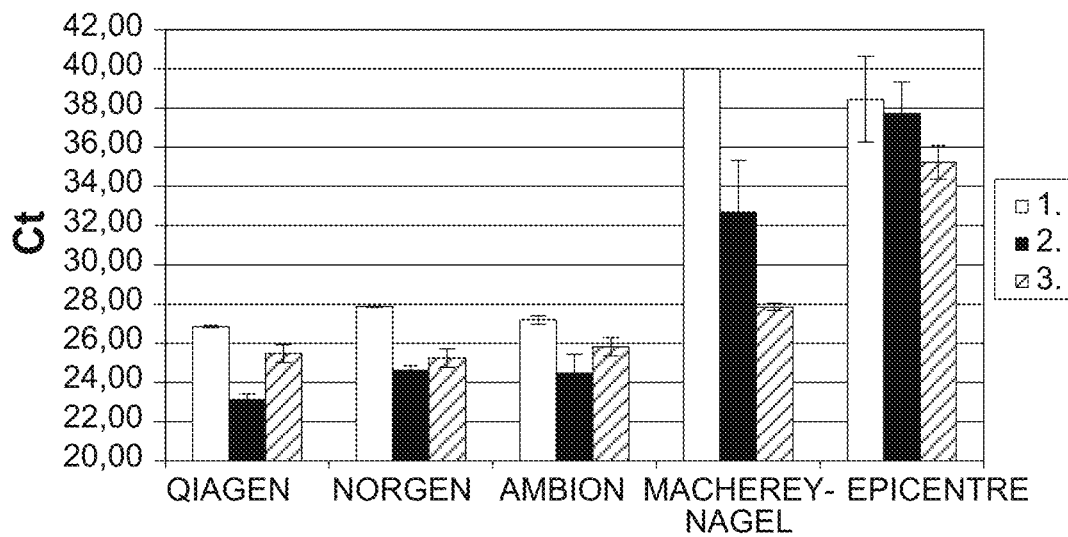
In FIG. 9a, for all samples the same template volumina, in FIG. 9b the same template concentrations have been used.
Figure 9B:
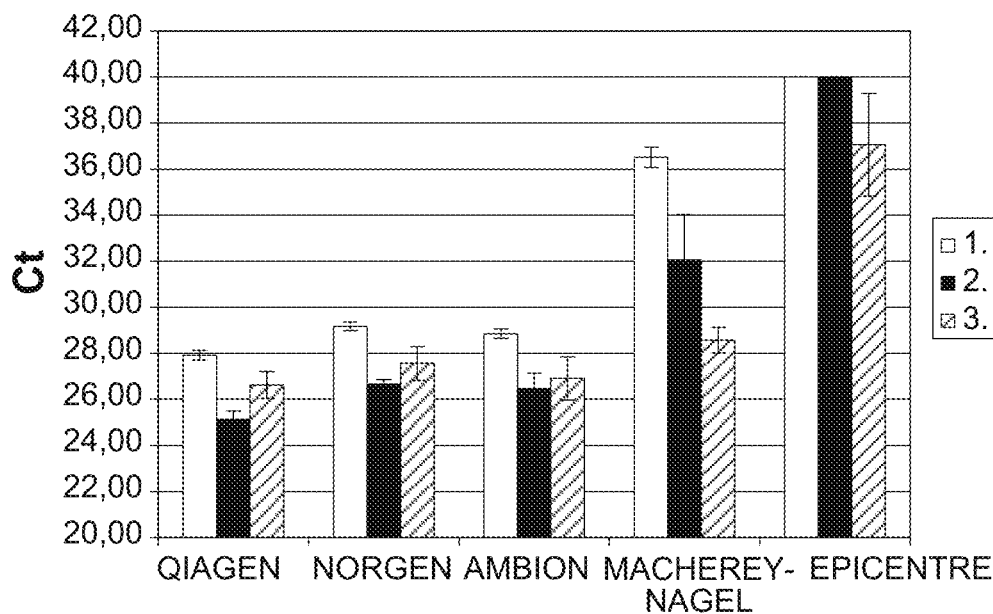

The isolated RNA was subjected to quantitative real-time-RT-PCR in order to analyse the advantageous effects of the method according to the present invention on the yield of a specific small RNAs. For this purpose, 20 ng of each isolated total RNA were used for detecting an amplicon of the microRNA miR29a, according to the procedure and devices described in example 1. The mean values (derived from triplets) of the measured ct-values were determined and the results are shown in FIG. 7. The results show that using the method according to the present invention leads to ct-values which are considerably lower than the ct-values of samples obtained by methods based on prior art kit protocols. These lower ct-values achieved with the method according to the present invention are attributable to the fact that the correspondingly isolated total RNA comprises larger amounts of the microRNA miR29a. Once again, these results demonstrate that the total RNA isolated according to the method of the present invention comprises more small nucleic acids, i.e. the yield of small nucleic acids from biological samples is increased. The methods based on prior art kit protocols are less efficient in rebinding the small target nucleic acids than the method according to the present invention.

The isolated DNA was subjected to quantitative real-time-PCR. For prion 78 bp, the mean values (derived from triplets) of the measured ct-values were determined and are summarised in FIG. 8a and b for equal volumes and equal concentrations respectively of the DNA samples used. Also for prion 78 bp, the ct-values are considerably lower using the method according to the present invention.

The isolated RNA was further subjected to quantitative real-time-RT-PCR. For Madh7, the mean values (derived from triplets) of the measured ct-values were determined and are summarised in FIG. 9a and b for equal volumes and equal concentrations respectively of the RNA samples used. The ct-values for the Madh7 are considerably lower using the method according to the present invention.

The invention claimed is:

1. A method for isolating target nucleic acids, including small target nucleic acids having lengths of less than 500 nucleotides, from a sample, comprising:
   a) binding at least a portion of the target nucleic acids, including small target nucleic acids having lengths of less than 500 nucleotides, to a first nucleic acid binding solid phase comprised in a column by passing the sample through said column,
   b) performing an enzymatic and/or chemical treatment on the first nucleic acid binding solid phase while the target nucleic acids are bound to said first nucleic acid binding solid phase, wherein the chemical treatment is a target nucleic acid modification treatment,
   c) collecting a portion of the small target nucleic acids released from the first nucleic acid binding solid phase during said treatment of step b) as flow-through while the remaining portion of target nucleic acids remains bound to said first nucleic acid binding solid phase,
   d) contacting said flow-through with a second nucleic acid binding solid phase in the presence of a recovery solution for the small target nucleic acids released from the first nucleic acid binding solid phase and contained in said flow-through to re-bind to said second nucleic acid binding solid phase, and
   e) optionally performing an elution of nucleic acids from the second nucleic acid binding solid phase.

2. The method of claim 1, wherein the first nucleic acid binding solid phase used in step a) is a membrane.

3. The method of claim 1, wherein the first nucleic acid binding solid phase is re-used in step d) as the second nucleic acid binding solid phase.

4. The method of claim 3, comprising, after step d), eluting
   (i) the target nucleic acids, including the small target nucleic acids, that become bound to the first nucleic acid binding solid phase in step a), and
   (ii) the small target nucleic acids that become re-bound to the first nucleic acid binding solid phase in step d) from the first nucleic acid binding solid phase.

5. The method of claim 1, wherein step c) is performed by passing a recovery solution through the first nucleic acid binding solid phase and collecting the flow-through.

6. The method of claim 5, wherein the first nucleic acid binding solid phase is re-used as the second nucleic acid binding solid phase in step d) for re-binding the small target nucleic acids contained in the flow-through to the first nucleic acid binding solid phase used in step a).

7. The method of claim 1, wherein the enzymatic and/or chemical treatment performed in step b) is selected from the group consisting of a nuclease digestion step, a protein digestion step, a lipase digestion step, and a target nucleic acid modification step.

8. The method of claim 1, wherein the enzymatic and/or chemical treatment performed in step b) involves conditions that result at least in a partial release of the target nucleic acids, including the small target nucleic acids, from the first nucleic acid binding solid phase.

9. The method of claim 1, wherein the recovery solution has one or more of the following characteristics:
   (a) it provides conditions suitable for binding small nucleic acids to the second nucleic acid binding solid phase used in step d);
   (b) it provides stronger binding conditions for binding small nucleic acids than the binding conditions used in step a);
   (c) it provides conditions suitable for binding small RNA to the nucleic acid binding solid phase used in step d);
   (d) it provides conditions suitable for binding small DNA to the nucleic acid binding solid phase used in step d);
   (e) it comprises at least one chaotropic agent and/or at least one alcohol; and/or it comprises at least one chaotropic agent in a concentration of 0.1 to 6 M and/or at least one alcohol selected from the group consisting of ethanol and isopropanol in a concentration of at least 50% v/v; and/or wherein binding conditions are used in step d) that have one or more of the following characteristics:
(A) they are suitable for binding small nucleic acids to the second nucleic acid binding solid phase used in step d);
(B) they provide stronger binding conditions for binding small nucleic acids than the binding conditions used in step a);
(C) they are suitable for binding small RNA to the second nucleic acid binding solid phase used in step d);
(D) they are suitable for binding small DNA to the second nucleic acid binding solid phase used in step d);
(E) they comprise at least one chaotropic agent and/or at least one alcohol; and/or
(F) they comprise at least one chaotropic agent in a concentration of 0.1 to 6 M and/or at least one alcohol selected from the group consisting of ethanol and isopropanol in a concentration of at least 50 % v/v.

10. The method of claim 9, wherein the concentration of the at least one chaotropic agent in characteristic (f) and/or characteristic (F) is 0.5 to 6 M.

11. The method of claim 1, wherein in step b) a DNase digest is performed if the target nucleic acid is RNA or an RNase digest is performed if the target nucleic acid is DNA.

12. The method of claim 1, wherein in step a) binding is performed under conditions having one or more of the following characteristics:
    a) the conditions are suitable for binding total nucleic acids to the first nucleic acid binding solid phase;
    b) the conditions are suitable for binding total RNA including small RNAs to the first nucleic acid binding solid phase;
    c) the conditions are suitable for binding total DNA including small DNAs to the first nucleic acid binding solid phase; and/or
    d) binding occurs in the presence of at least one chaotropic agent and/or at least one alcohol.

13. The method of claim 1, wherein the sample is lysed or processed prior to or during step a).

14. The method of claim 1, wherein the small target nucleic acids comprise degraded nucleic acids.

15. The method of claim 1, wherein the sample is selected from and/or is derived from a sample selected from the group consisting of cells, clinical samples, body fluids, tissue, blood, blood products, plants, bacteria, viruses, fungi, human and animal sample material, environmental samples, isolated nucleic acids, lysates, eluates, fixed samples, cross-linked samples, and FFPE samples.

16. The method of claim 1, wherein the small nucleic acids comprise non-degraded small nucleic acids.

17. The method of claim 1, wherein the small target nucleic acids have lengths of less than 300 nucleotides, less than 250 nucleotides, less than 200 nucleotides, less than 100 nucleotides, or less than 70 nucleotides.

18. The method of claim 1, wherein the small target nucleic acids are selected from miRNA, siRNA, snoRNAs, snRNAs, tRNA, piRNA, tnRNA, small rRNA, hnRNA, circulating nucleic acids, fragments of genomic DNA or RNA, degraded nucleic acids, ribozymes, viral RNA or DNA, and nucleic acids of infectious origin.

19. method for isolating target nucleic acids, including small target nucleic acids having lengths of less than 500 nucleotides, from a sample, comprising:
    a) binding at least a portion of the target nucleic acids, including small target nucleic acids having lengths of less than 500 nucleotides, to a nucleic acid binding membrane by passing the sample through said membrane,
    b) performing an enzymatic treatment or a chemical target nucleic acid modification treatment involving an aqueous solution on the membrane while the target nucleic acids are bound to said membrane,
    c) passing a recovery solution through said membrane and collecting the flow-through that comprises the small target nucleic acids,
    d) passing said flow-through through the membrane of step a) for re-binding the small target nucleic acids contained in the flow-through to said membrane, and
    e) optionally eluting the target nucleic acids, including the small nucleic acids, from said membrane.

20. The method of claim 19, wherein the small target nucleic acids have lengths of less than 300 nucleotides, less than 250 nucleotides, less than 200 nucleotides, less than 100 nucleotides, or less than 70 nucleotides.

21. The method of claim 19, wherein the small target nucleic acids are selected from miRNA, siRNA, snoRNAs, snRNAs, tRNA, piRNA, tnRNA, small rRNA, hnRNA, circulating nucleic acids, fragments of genomic DNA or RNA, degraded nucleic acids, ribozymes, viral RNA or DNA, and nucleic acids of infectious origin.

22. A method of re-binding small nucleic acids having lengths less than 500 nucleotides to a nucleic acid binding membrane, wherein the small nucleic acids were bound to the membrane, but subsequently released during an on-membrane enzymatic treatment or a chemical target nucleic acid modification treatment, comprising:
    A) a) passing a recovery solution through the membrane and collecting the flow-through that comprises the small nucleic acids, and
       b) passing the flow-through through the membrane, thereby re-binding the small nucleic acids to the membrane; or
    B) a) collecting a flow-through of the on-membrane treatment,
       b) adding a recovery solution to the flow-through to form a mixture,
       c) passing the mixture of step B) b) through the membrane, thereby re-binding the small nucleic acids to the membrane.

23. The method of claim 22, wherein at least a portion of the small nucleic acids are located beneath the membrane after they were released from said membrane.

24. The method of claim 22, the recovery solution has one or more of the characteristics:
    (a) it provides conditions suitable for binding small nucleic acids to the membrane;
    (b) it provides stronger binding conditions for binding small nucleic acids than the binding conditions under which the small nucleic acids were bound to the membrane;
    (c) it provides conditions suitable for binding small RNA to the membrane;
    (d) it provides conditions suitable for binding small DNA to the membrane;
    (e) it comprises at least one chaotropic agent and/or at least one alcohol; and/or
    (f) it comprises at least one chaotropic agent in a concentration of 0.1 to 6 M and/or at least one alcohol selected from the group consisting of ethanol and isopropanol in a concentration of at least 50% v/v.

25. The method of claim 24, wherein the concentration of the at least one chaotropic agent in characteristic (f) is 0.5 to 6 M.

26. The method of claim 22, wherein the small nucleic acids have lengths of less than 300 nucleotides, less than 250 nucleotides, less than 200 nucleotides, less than 100 nucleotides, or less than 70 nucleotides.

27. The method of claim 22, wherein the small nucleic acids are selected from miRNA, siRNA, snoRNAs, snRNAs, tRNA, piRNA, tnRNA, small rRNA, hnRNA, circulating nucleic acids, fragments of genomic DNA or RNA, degraded nucleic acids, ribozymes, viral RNA or DNA, and nucleic acids of infectious origin.

* * * * *